United States Patent
Kim et al.

(10) Patent No.: US 12,245,828 B2
(45) Date of Patent: *Mar. 11, 2025

(54) SYSTEMS AND METHODS FOR FACILITATING ROBOTIC SURGICAL PROCEDURES

(71) Applicant: GLOBUS MEDICAL, INC., Audubon, PA (US)

(72) Inventors: Albert Kim, San Diego, CA (US); Gregory Pellegrino, San Diego, CA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/425,452

(22) Filed: Jan. 29, 2024

(65) Prior Publication Data
US 2024/0206991 A1    Jun. 27, 2024

Related U.S. Application Data

(63) Continuation of application No. 17/696,203, filed on Mar. 16, 2022, now Pat. No. 11,918,308, which is a continuation of application No. PCT/US2020/052512, filed on Sep. 24, 2020.

(60) Provisional application No. 62/905,340, filed on Sep. 24, 2019, provisional application No. 62/905,379, filed on Sep. 24, 2019.

(51) Int. Cl.
| | | |
|---|---|---|
| G06F 3/048 | (2013.01) | |
| A61B 34/00 | (2016.01) | |
| A61B 34/10 | (2016.01) | |
| A61B 34/20 | (2016.01) | |
| A61B 34/37 | (2016.01) | |
| G06F 3/04817 | (2022.01) | |
| G06F 3/0484 | (2022.01) | |
| G06F 3/033 | (2013.01) | |

(52) U.S. Cl.
CPC .............. *A61B 34/25* (2016.02); *A61B 34/10* (2016.02); *A61B 34/20* (2016.02); *A61B 34/37* (2016.02); *G06F 3/04817* (2013.01); *G06F 3/0484* (2013.01); *A61B 2034/102* (2016.02); *A61B 2034/105* (2016.02); *A61B 2034/107* (2016.02); *A61B 2034/252* (2016.02); *A61B 2034/254* (2016.02); *G06F 3/0334* (2013.01)

(58) Field of Classification Search
CPC ... G06F 3/04817; G06F 3/0484; A61B 34/25; A61B 34/10; A61B 34/20; A61B 34/34
See application file for complete search history.

(56) References Cited

U.S. PATENT DOCUMENTS

| | | | | |
|---|---|---|---|---|
| 9,283,048 B2 * | 3/2016 | Kostrzewski | .......... | A61B 34/37 |
| 9,681,982 B2 * | 6/2017 | Yacono | ................ | G02B 27/017 |
| 11,147,636 B2 * | 10/2021 | Hallen | ................ | H04N 13/324 |
| 11,645,467 B2 * | 5/2023 | Seaton | ................ | G06F 40/295 |
| | | | | 382/159 |

(Continued)

OTHER PUBLICATIONS

Russell H. Taylor, A Perspective on Medical Robotics, 2006, IEEE, 13 pages. (Year: 2006).*

(Continued)

*Primary Examiner* — Linh K Pham

(57) ABSTRACT

Disclosed herein are systems and methods for using a robotic surgical system comprising a GUI and a robotic arm.

18 Claims, 28 Drawing Sheets

(56) References Cited

U.S. PATENT DOCUMENTS

| | | | | |
|---|---|---|---|---|
| 11,754,853 | B2* | 9/2023 | Fuerst | G02B 27/0093 |
| | | | | 348/51 |
| 11,832,901 | B2* | 12/2023 | Hallen | A61B 90/37 |
| 12,070,280 | B2* | 8/2024 | Charles | A61B 34/25 |
| 2006/0142657 | A1* | 6/2006 | Quaid | A61B 90/37 |
| | | | | 600/424 |
| 2009/0275929 | A1* | 11/2009 | Zickler | A61B 3/113 |
| | | | | 606/4 |
| 2013/0217967 | A1* | 8/2013 | Mohr | A61B 34/37 |
| | | | | 600/109 |
| 2014/0005555 | A1* | 1/2014 | Tesar | A61B 1/00193 |
| | | | | 600/476 |
| 2015/0025547 | A1* | 1/2015 | Hannaford | A61B 34/76 |
| | | | | 606/130 |
| 2015/0173846 | A1* | 6/2015 | Schneider | A61B 1/00042 |
| | | | | 600/424 |
| 2015/0366624 | A1* | 12/2015 | Kostrzewski | A61M 29/00 |
| | | | | 606/130 |
| 2018/0132949 | A1* | 5/2018 | Merette | G06T 11/60 |
| 2018/0368930 | A1* | 12/2018 | Esterberg | G06T 17/00 |
| 2019/0000570 | A1* | 1/2019 | Esterberg | A61B 34/20 |
| 2019/0099226 | A1* | 4/2019 | Hallen | A61B 34/10 |
| 2019/0183591 | A1* | 6/2019 | Johnson | B25J 9/1666 |
| 2019/0274775 | A1* | 9/2019 | Olive | A61B 34/32 |
| 2019/0327394 | A1* | 10/2019 | Ramirez Luna | H04N 23/51 |
| 2020/0008884 | A1* | 1/2020 | Lavallee | A61B 34/25 |
| 2020/0012116 | A1* | 1/2020 | Fuerst | G06F 3/012 |
| 2020/0268452 | A1* | 8/2020 | Rezach | A61B 34/30 |
| 2020/0383803 | A1* | 12/2020 | Wu | A61B 6/5217 |
| 2021/0030499 | A1* | 2/2021 | Peine | A61B 90/361 |
| 2021/0192759 | A1* | 6/2021 | Lang | A61B 90/98 |
| 2022/0265373 | A1* | 8/2022 | Kim | G06F 3/0482 |

OTHER PUBLICATIONS

Li et al., Attention-aware robotic laparoscope for human-robot cooperative surgery, 2013, 6 pages. (Year: 2013).*

Frank Bova, Computer Based Guidance in the Modern Operating Room: A Historical Perspective, 2010, IEEE, 14 pages. (Year: 2010).*

* cited by examiner

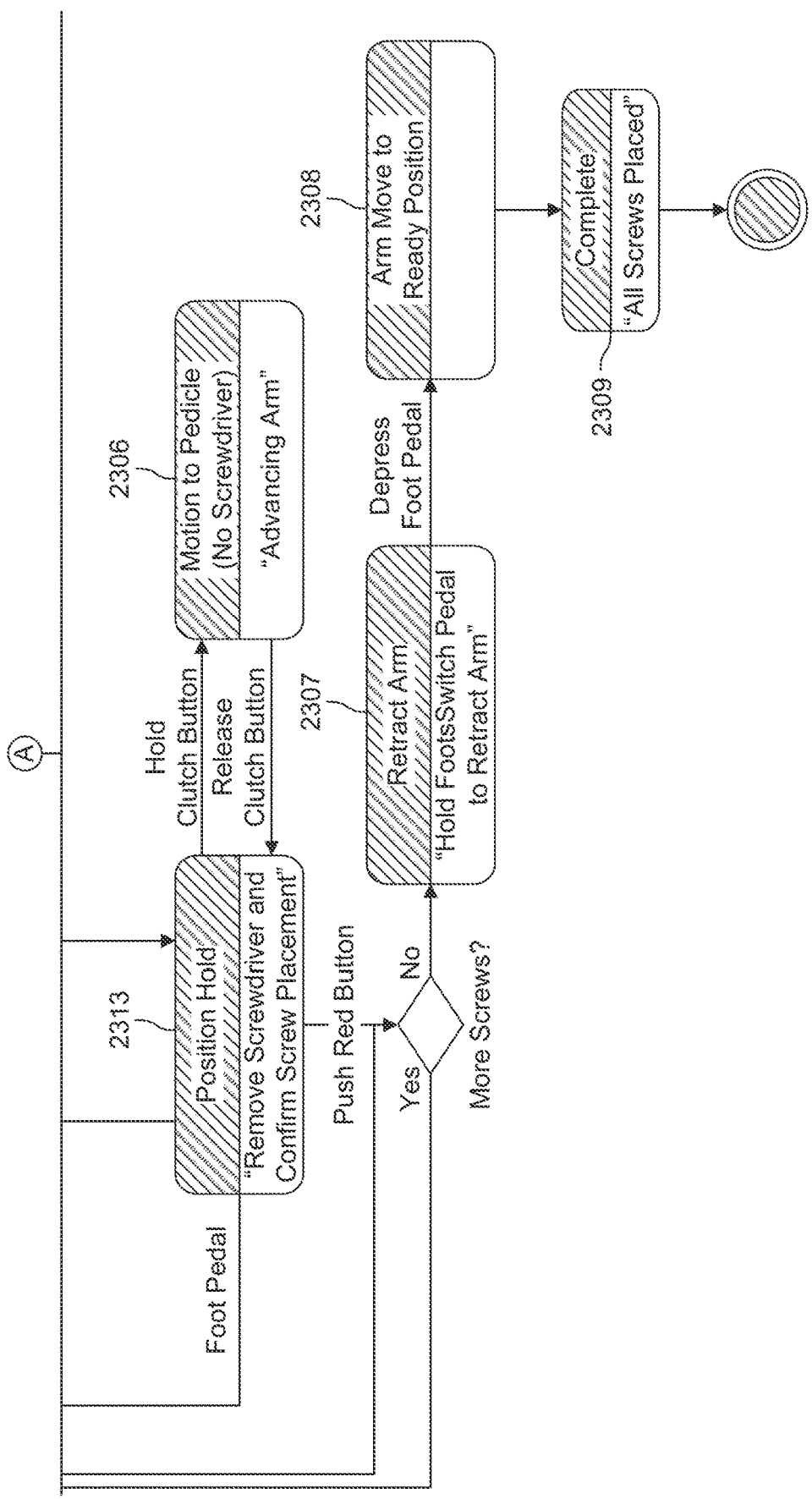
FIG. 23 (Continue)

SYSTEMS AND METHODS FOR FACILITATING ROBOTIC SURGICAL PROCEDURES

CROSS-REFERENCE TO RELATED APPLICATIONS

This application is a continuation of U.S. patent application Ser. No. 17/696,203 filed on Mar. 16, 2022, which is a continuation of PCT Application No. PCT/US2020/052512, filed Sep. 24, 2020 which is a non-provisional of, and claims the benefit of, U.S. Provisional patent application Ser. Nos. 62/905,340 filed Sep. 24, 2019 and 62/905,379 filed on Sep. 24, 2019, the entire contents of which are hereby expressly incorporated by reference into this disclosure as if set forth in its entirety herein.

BACKGROUND

Robotic surgical systems or robot-assisted surgery systems utilize a robotic arm to perform surgical procedures automatically or semi-automatically under the control of a surgeon. Robotic surgical systems can be used in minimally invasive surgery (MIS) which involves small surgical incisions that reduce surgeon's visualization of patient anatomy and three dimensional (3D) spatial awareness in comparison to traditional "open" techniques.

SUMMARY

Robotic surgery or robot-assisted surgery may allow surgeon to perform complex surgical procedures with more precision, flexibility, and control than that with conventional techniques. With the robotic arm, surgeons maybe capable of performing delicate and complex procedures that is difficult or impossible with traditional methods. However, surgeries involving a robotic arm may present various challenges. For example, prompt feedback from the robot or other elements of the surgical system can be necessary for the surgeon to make informed movement and avoid inaccuracy or mistakes in the surgery. Additionally, in an ongoing surgical procedure, figuring out when, how, and where to interact with the robotic arm and other control features of the robotic surgical system may cause distraction, delay, inaccuracy, and unnecessary stress to the personnel involved. Thus, there is an urgent and unmet need for hardware and/or software that can help the surgeon interact conveniently and efficiently with the robotic arm, maximize the benefit of the robotic surgery and minimize possible adverse event.

Disclosed herein are robotic surgical systems that utilizes a graphical user interface (GUI) to facilitate effective and efficient interaction between the surgeon and the robotic arm. The advantage of the robotic surgical systems disclosed herein include enabling direct visualization of the surgical site and the moving surgical tools so as to provide direct, accurate and instantaneous feedback to the surgeon on the motion of the robotic arms. Another advantage of the robotic surgical system disclosed herein is allowing the surgeon to track different aspects of the surgery simultaneously by providing graphical and/or text information, color coding, and various forms of visual and/or audio cues. Yet another advantage is providing instantaneous instructions to the surgeon as to how and when to interact with the robotic arm to transition the surgical procedure smoothly between different stages or steps.

In one aspect, disclosed herein are methods for using a robotic surgical system, the method comprising: displaying a first image of a surgical site on a digital display using a graphical user interface (GUI), wherein the first image includes an anatomical structure of a patient with a first orientation; superimposing a representation of a surgical tool on the anatomical structure in the first image using the GUI, wherein the representation includes color coding; at one or more stages of a surgical procedure: displaying a status indicator bar using the GUI, wherein the status indicator bar comprises a first icon including instructive information related to the surgical tool; allowing a user to interact directly with the first icon based on the instructive information or allowing a user to provide an input to the robotic surgical system related to operation of the surgical tool based on the instructive information; allowing a robotic arm to automatically move, approach the surgical tool, or move the surgical tool, based on the user interaction directly with the first icon at the GUI, the input provided by the user, or both until a pre-determined stopping criterion is met; providing an audio cue, a visual cue, or both simultaneously to a user when the user is providing the input, the robotic arm is moving, or both; and prompting the user to a subsequent stage of the surgical procedure by updating the first icon at the status indicator bar using the GUI if a status change criterion has been met.

In another aspect, disclosed herein are methods for using a robotic surgical system, the method comprising: displaying a first image and a second image of a surgical site on a digital display using a graphical user interface (GUI), wherein the first image and the second image include an anatomical structure of a patient with different orientations; superimposing a representation of a surgical tool on the anatomical structure in the first image and the second image using the GUI, wherein the representation includes color coding; at one or more stages of a surgical procedure: displaying a status indicator bar using the GUI, wherein the status indicator bar comprises a first icon including instructive information related to the surgical tool; displaying a second icon using the GUI, the second icon including status information of the surgical procedure related to the one or more stages of the surgical procedure; allowing a user to interact directly with the first icon based on the instructive information or allowing a user to provide an input to the robotic surgical system related to operation of the surgical tool based on the instructive information; allowing a robotic arm to automatically move, approach the surgical tool, or move the surgical tool, based on the user interaction directly with the first icon at the GUI, the input provided by the user, or both until a pre-determined stopping criterion is met; providing an audio cue, a visual cue, or both simultaneously to a user when the user is providing the input, the robotic arm is moving, or both; and prompting the user to a subsequent stage of the surgical procedure by updating the first icon, the second icon or both at the status indicator bar using the GUI if a status change criterion has been met. In some cases, the surgical tool is superimposed on the anatomical structure in full dimension and at a pre-determined opacity. In some cases, the color coding comprises different colors for on-going, planned, and completed operation. In some cases, the instructive information includes the color coding. In some cases, the instructive information includes an operation of the surgical tool to be conducted. In some cases, the instructive information includes graphical information or text related to selection or confirmation of a location, size, type of the surgical tool, or a combination thereof. In some cases, the instructive information prompts the user to select or confirm location, size, type of the surgical tool, or a combination thereof. In some cases, allowing the user to interact directly with the first icon based on the instructive information comprises: allowing the user to interact with the GUI using a first input device; allowing the interaction to be reflected on the digital display; and allowing the interaction to be communicated to a digital processing device of the robotic surgical system or the robotic arm. In some cases, the instructive information prompts the user to start operation of the surgical tool. In some cases, allowing the user to provide an input to the robotic surgical system related to operation of the surgical tool in the surgical procedure based on the instructive information: allowing the user to provide the input at an actuation element using a second input device; optionally allowing the input to be reflected on the digital display; and allowing the input to be communicated to a digital processing device of the robotic surgical system or the robotic arm. In some cases, the second input device includes a foot pedal. In some cases, the input includes depression of the foot pedal. In some cases, the pre-determined stopping criterion comprises one or more of: a distance of at least a portion of the robotic arm to a reference point, wherein the reference point is at the anatomical structure of the patient, a patient reference array, or a tool tracking array. In some cases, the status information includes the color coding. In some cases, the status information includes a list of trajectories and status of surgical operation on the trajectories. In some cases, the visual cue includes a representation of the robotic arm in the first image, the second image, or both, and wherein the representation is continuously updated based on the location or movement of the robotic arm. In some cases, the visual cue includes alternating color signal at the digital display when the robotic arm is in motion and static color signal when the robotic arm completes the motion. In some cases, the audio cue includes alternating or static sound. In some cases, the representation of the surgical tool comprises representation of more than one surgical tool, and wherein the more than one surgical tool includes a surgical tool that has been placed and a surgical tool that has been planned. In some embodiments, the method disclosed herein further comprises activating a skive detection unit and displaying a skive detection icon at the one or more stage of the surgical procedure, wherein the skive detection icon is color coded and includes a graphical meter that reflects level of skive at the skive detection unit. Alternative embodiments to reflect level of skive may include: display of force/torque along one or more directions relative to the patient, display of existence or non-existence of skive level by comparing the force/torque to a threshold that may be specific to the surgical procedure, visual, audio, or other types of warnings to the user when skive level is above a pre-determined threshold or warning level. In some cases, updating the first icon includes updating the instructive information and wherein updating the second icon includes updating the status information. In some cases, prompting the user to the subsequent stage of the surgical procedure comprises updating the first image, the second image, the representation of the surgical tool, or a combination thereof.

In yet another aspect, disclosed herein are robotic surgical systems comprising: a digital processing device comprising a processor, a memory, an operating system configured to perform executable instructions, a computer program including instructions executable by the digital processing device to create a graphical user interface (GUI) that is interactive with a user, and a digital display to display the GUI to the user, wherein the GUI comprises a first image of a surgical site, the first image including an anatomical structure of a patient with a first orientation, and wherein the GUI further comprises a representation of a surgical tool superimposed on the anatomical structure in the first image, the representation including color coding, wherein the GUI comprises a status indicator bar, wherein the status indicator bar includes a first icon including instructive information related to the surgical tool, wherein the GUI is configured to allow the user to interact directly with the first icon based on the instructive information or provide an input related to operation of the surgical tool based on the instructive information, and wherein the GUI is configured to provide an audio cue, a visual cue, or both simultaneously to the user based on the user's input, and configured to prompt the user to a next stage of the surgical procedure by changing the first icon if a status change criterion has been met; and a robotic arm in communication with the digital processing device, wherein the robotic arm is controlled by the digital processing device to automatically move, approach the surgical tool, or move the surgical tool, based on the input provided by the user at the GUI until a pre-determined stopping criterion is met.

In yet another aspect, disclosed herein are robotic surgical systems comprising: a digital processing device comprising a processor, a memory, an operating system configured to perform executable instructions, a computer program including instructions executable by the digital processing device to create a graphical user interface (GUI) that is interactive with a user, and a digital display to display the GUI to the user, wherein the GUI comprises a first image and a second image of a surgical site, the first image and the second image including an anatomical structure of a patient with different orientations, and wherein the GUI further comprises a representation of a surgical tool superimposed on the anatomical structure in the first image and the second image, the representation including color coding, wherein the GUI comprises a status indicator bar, wherein the status indicator bar includes a first icon including instructive information related to the surgical tool and a second icon including status information of a surgical procedure using the surgical tool, wherein the GUI is configured to allow the user to interact directly with the first icon based on the instructive information or provide an input related to operation of the surgical tool based on the instructive information, and wherein the GUI is configured to provide an audio cue, a visual cue, or both simultaneously to the user based on the user's input, and configured to prompt the user to a next stage of the surgical procedure by changing the first icon, the second icon, or both if a status change criterion has been met; and a robotic arm in communication with the digital processing device, wherein the robotic arm is controlled by the digital processing device to automatically move, approach the surgical tool, or move the surgical tool, based on the input provided by the user at the GUI until a pre-determined stopping criterion is met.

Disclosed herein are systems and methods for registering a robotic arm to medical images containing a surgical site of a subject and one or more surgical tools in three-dimensions. Disclosed herein are systems and methods for registering movement of a robotic arm to a coordinate system of medical images containing a surgical site of a subject and one or more surgical tools in three-dimensions and/or coordinate system of tracking arrays. The systems and methods herein can be advantageously utilized for three-dimensional (3D) navigation of the surgical tools in real-time and operation of the surgical tools in robotic surgeries.

In yet another aspect, disclosed herein is a method for registering a robotic arm to medical images containing a surgical site of a subject and one or more surgical tools in three-dimensions, the method comprising: providing a robotic surgical system to a user, the robotic surgical system comprising a robotic arm with a base, a first tracking array configured to be attached to an anatomical feature of the subject, a second tracking array configured to be attached at or near a distal end of the robotic arm, optionally a first image capturing device, optionally a second image capturing device, and optionally a digital processing device, wherein the first image capturing device is configured to image the anatomical feature of the subject optionally for navigating the one or more surgical tools during a surgical operation, wherein the second image capturing device is configured to track the first and the second tracking arrays, wherein the first and the second tracking arrays comprise one or more tracking marker detectable by the second image capturing device; allowing the user to track the robotic arm in a base coordinate system by determining a relative location of the robotic arm to the base of the robotic arm, wherein the base of the robotic arm is fixed relative to the second image capturing device; allowing the user to track the robotic arm in a tracking coordinate system by tracking the second tracking array using the second image capturing device; allowing the user to obtain three-dimensional registration information of the tracking coordinate system and an image coordinate system, the image coordinate system determined by the first image capturing device; allowing the user to register the base coordinate system with the tracking coordinate system thereby a pre-determined translation, rotation, or both of the robotic arm in the tracking coordinate system or the image coordinate system is transformed to a transformed translation, rotation, or both relative to the base of the robotic arm; and optionally allowing the user to control movement of the robotic arm by the pre-determined translation, rotation, or both in the tracking coordinate system via the transformed translation, rotation, or both relative to the base.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
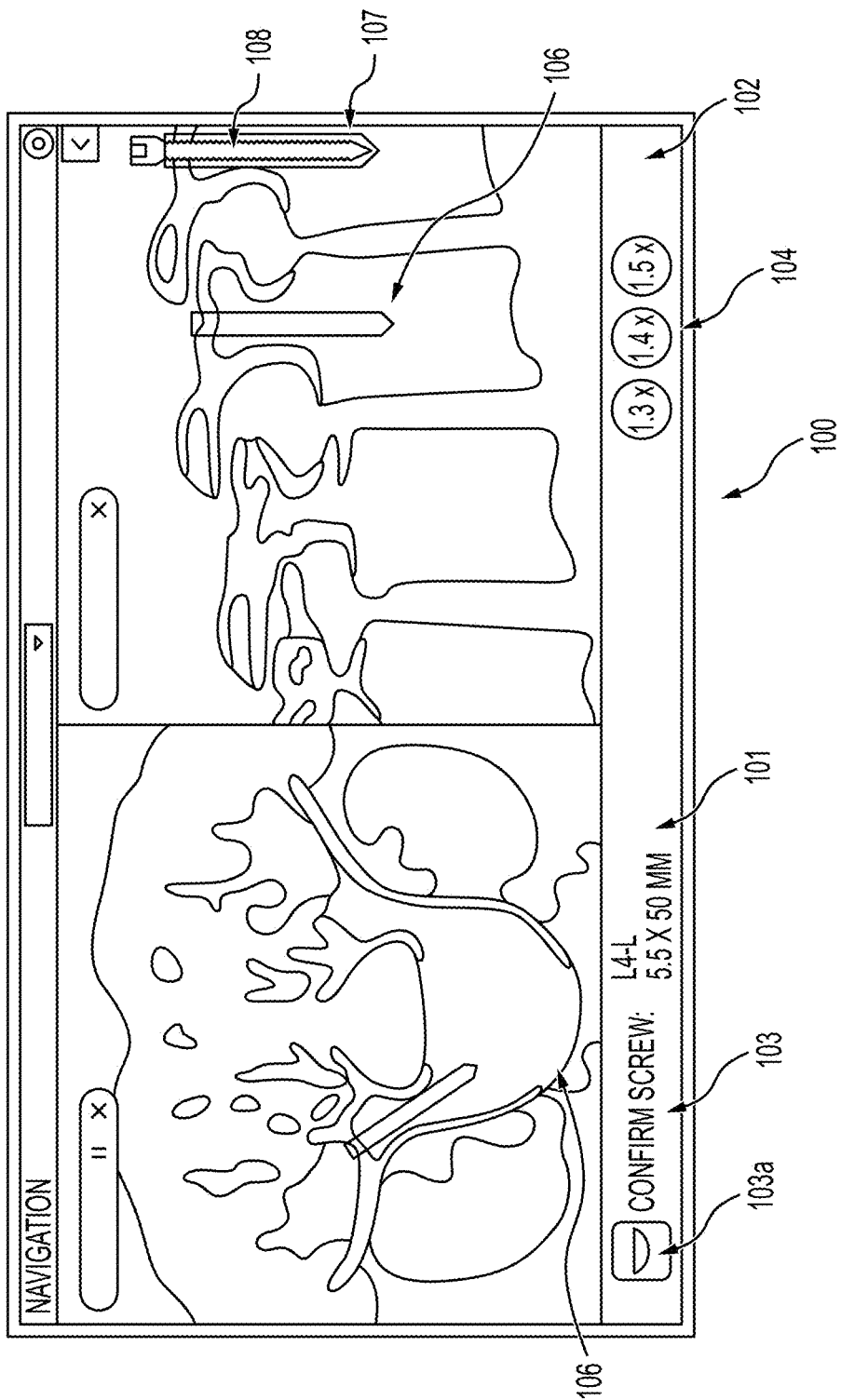
FIG. 1 shows an exemplary embodiment of the graphical user interface (GUI) herein; in this case, customization of the GUI, in accordance with embodiments herein.

Disclosed herein, in some embodiments, are methods for using a robotic surgical system, the method comprising: displaying a first image of a surgical site on a digital display using a graphical user interface (GUI), wherein the first image includes an anatomical structure of a patient with a first orientation; superimposing a representation of a surgical tool on the anatomical structure in the first image using the GUI, wherein the representation includes color coding; at one or more stages of a surgical procedure: displaying a status indicator bar using the GUI, wherein the status indicator bar comprises a first icon including instructive information related to the surgical tool; allowing a user to interact directly with the first icon based on the instructive information or allowing a user to provide an input to the robotic surgical system related to operation of the surgical tool based on the instructive information; allowing a robotic arm to automatically move, approach the surgical tool, or move the surgical tool, based on the user interaction directly with the first icon at the GUI, the input provided by the user, or both until a predetermined stopping criterion is met; providing an audio cue, a visual cue, or both simultaneously to a user when the user is providing the input, the robotic arm is moving, or both; and prompting the user to a subsequent stage of the surgical procedure by updating the first icon at the status indicator bar using the GUI if a status change criterion has been met.

Disclosed herein, in some embodiments, are methods for using a robotic surgical system, the method comprising: displaying a first image and a second image of a surgical site on a digital display using a graphical user interface (GUI), wherein the first image and the second image include an anatomical structure of a patient with different orientations; superimposing a representation of a surgical tool on the anatomical structure in the first image and the second image using the GUI, wherein the representation includes color coding; at one or more stages of a surgical procedure: displaying a status indicator bar using the GUI, wherein the status indicator bar comprises a first icon including instructive information related to the surgical tool; displaying a second icon using the GUI, the second icon including status information of the surgical procedure related to the one or more stages of the surgical procedure; allowing a user to interact directly with the first icon based on the instructive information or allowing a user to provide an input to the robotic surgical system related to operation of the surgical tool based on the instructive information; allowing a robotic arm to automatically move, approach the surgical tool, or move the surgical tool, based on the user interaction directly with the first icon at the GUI, the input provided by the user, or both until a pre-determined stopping criterion is met; providing an audio cue, a visual cue, or both simultaneously to a user when the user is providing the input, the robotic arm is moving, or both; and prompting the user to a subsequent stage of the surgical procedure by updating the first icon, the second icon or both at the status indicator bar using the GUI if a status change criterion has been met. In some cases, the surgical tool is superimposed on the anatomical structure in full dimension and at a pre-determined opacity. In some cases, the color coding comprises different colors for on-going, planned, and completed operation. In some cases, the instructive information includes the color coding. In some cases, the instructive information includes an operation of the surgical tool to be conducted. In some cases, the instructive information includes graphical information or text related to selection or confirmation of a location, size, type of the surgical tool, or a combination thereof. In some cases, the instructive information prompts the user to select or confirm location, size, type of the surgical tool, or a combination thereof. In some cases, allowing the user to interact directly with the first icon based on the instructive information comprises: allowing the user to interact with the GUI using a first input device; allowing the interaction to be reflected on the digital display; and allowing the interaction to be communicated to a digital processing device of the robotic surgical system or the robotic arm. In some cases, the instructive information prompts the user to start operation of the surgical tool. In some cases, allowing the user to provide an input to the robotic surgical system related to operation of the surgical tool in the surgical procedure based on the instructive information: allowing the user to provide the input at an actuation element using a second input device; optionally allowing the input to be reflected on the digital display; and allowing the input to be communicated to a digital processing device of the robotic surgical system or the robotic arm. In some cases, the second input device includes a foot pedal. In some cases, the input includes depression of the foot pedal. In some cases, the pre-determined stopping criterion comprises one or more of: a distance of at least a portion of the robotic arm to a reference point, wherein the reference point is at the anatomical structure of the patient, a patient reference array, or a tool tracking array. In some cases, the status information includes the color coding. In some cases, the status information includes a list of trajectories and status of surgical operation on the trajectories. In some cases, the visual cue includes a representation of the robotic arm in the first image, the second image, or both, and wherein the representation is continuously updated based on the location or movement of the robotic arm. In some cases, the visual cue includes alternating color signal at the digital display when the robotic arm is in motion and static color signal when the robotic arm completes the motion. In some cases, the audio cue includes alternating or static sound. In some cases, the representation of the surgical tool comprises representation of more than one surgical tool, and wherein the more than one surgical tool includes a surgical tool that has been placed and a surgical tool that has been planned. In some embodiments, the method disclosed herein further comprises activating a skive detection unit and displaying a skive detection icon at the one or more stage of the surgical procedure, wherein the skive detection icon is color coded and includes a graphical meter that reflects level of skive at the skive detection unit. In some cases, updating the first icon includes updating the instructive information and wherein updating the second icon includes updating the status information. In some cases, prompting the user to the subsequent stage of the surgical procedure comprises updating the first image, the second image, the representation of the surgical tool, or a combination thereof.

Disclosed herein, in some embodiments, are robotic surgical systems comprising: a digital processing device comprising a processor, a memory, an operating system configured to perform executable instructions, a computer program including instructions executable by the digital processing device to create a graphical user interface (GUI) that is interactive with a user, and a digital display to display the GUI to the user, wherein the GUI comprises a first image of a surgical site, the first image including an anatomical structure of a patient with a first orientation, and wherein the GUI further comprises a representation of a surgical tool superimposed on the anatomical structure in the first image, the representation including color coding, wherein the GUI comprises a status indicator bar, wherein the status indicator bar includes a first icon including instructive information related to the surgical tool, wherein the GUI is configured to allow the user to interact directly with the first icon based on the instructive information or provide an input related to operation of the surgical tool based on the instructive information, and wherein the GUI is configured to provide an audio cue, a visual cue, or both simultaneously to the user based on the user's input, and configured to prompt the user to a next stage of the surgical procedure by changing the first icon if a status change criterion has been met; and a robotic arm in communication with the digital processing device, wherein the robotic arm is controlled by the digital processing device to automatically move, approach the surgical tool, or move the surgical tool, based on the input provided by the user at the GUI until a pre-determined stopping criterion is met.

Disclosed herein, in some embodiments, are robotic surgical systems comprising: a digital processing device comprising a processor, a memory, an operating system configured to perform executable instructions, a computer program including instructions executable by the digital processing device to create a graphical user interface (GUI) that is interactive with a user, and a digital display to display the GUI to the user, wherein the GUI comprises a first image and a second image of a surgical site, the first image and the second image including an anatomical structure of a patient with different orientations, and wherein the GUI further comprises a representation of a surgical tool superimposed on the anatomical structure in the first image and the second image, the representation including color coding, wherein the GUI comprises a status indicator bar, wherein the status indicator bar includes a first icon including instructive information related to the surgical tool and a second icon including status information of a surgical procedure using the surgical tool, wherein the GUI is configured to allow the user to interact directly with the first icon based on the instructive information or provide an input related to operation of the surgical tool based on the instructive information, and wherein the GUI is configured to provide an audio cue, a visual cue, or both simultaneously to the user based on the user's input, and configured to prompt the user to a next stage of the surgical procedure by changing the first icon, the second icon, or both if a status change criterion has been met; and a robotic arm in communication with the digital processing device, wherein the robotic arm is controlled by the digital processing device to automatically move, approach the surgical tool, or move the surgical tool, based on the input provided by the user at the GUI until a pre-determined stopping criterion is met.

Certain Terms

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "and" or "or" herein is intended to encompass "and/or" unless otherwise stated.

Disclosed herein, the "user" is equivalent to a surgeon, a technician, or otherwise any medical professional that participate in a surgical procedure.

The medical procedure herein is equivalent to a medical operation, a surgical procedure, a surgical operation, and a surgery. The medical procedure can be a minimally invasive surgery. The medical procedure can include a spinal surgery. The medical procedure can include one or more of spinal fusion, decompression, alignment, disc replacement, corpectomy, and stabilization. The medical procedure can include one or more of pedicle screw placement, posterior lumbar interbody fusion (PLIF), transforaminal lumbar interbody fusion (TLIF), anterior lumbar interbody fusion (ALIF), and lateral interbody fusion (e.g. XLIF® by NuVasive, Inc. San Diego, CA).

GUIs

Disclosed herein are GUIs that can be displayed to a user, for example, on a digital display. The GUI can be used in a surgical procedure, e.g., robotic surgical procedure, to facilitate user interaction with other elements in a robotic surgical system, such as a robotic arm. The GUIs disclosed herein may efficiently present instructive information to the surgeon based on the status of the surgery, the GUI may also generate feedback to a surgical movement and direct visualization of the surgical tools thereby significantly reducing complexity of the surgical procedure and minimizing miscommunication that may lead to adverse events.

FIGS. 1-19 show different exemplary embodiment of the GUIs disclosed herein.

The GUI 100 herein can include a first image 101 of a surgical site in a first orientation, and optionally a second image 102 of the same surgical site but with a different orientation. The first and second images can be two-dimensional (2D) or three-dimensional (3D). The orientation of the images can be any arbitrary orientation in the 3D space. The first and second image can be obtained with different imaging modalities, such as X-ray, magnetic resonance imaging (MRI), Ultrasound, computer tomography (CT). The image can be a digital reconstructed radiograph (DRR) image. Non-limiting examples of the orientations can be axial view (e.g., FIG. 5), sagittal view (e.g., FIG. 5), and/or coronal view (e.g., FIG. 3).

In some embodiments, the GUI includes a status indicator bar that has multiple icons 103, 104, 105, 109 that are presented simultaneously to the user with the images and without interference to the presentation of images. In some embodiments, the icons are completely or partially superimposed or overlaid on part of the image(s). In some embodiments, some icons are immediately adjacent to the images, for example, below the images as shown in FIGS. 1-19.

An icon herein can include multiple parts, e.g., sub-icons. As shown in FIG. 1, the first icon 103 includes a part that has instructive text "confirm screw," and a second part that display the screw information—the screw is on the left side of the L4 vertebra, "L4-L" and the screw size is "5.5×50 mm." In this particular embodiment, the icon 103 may also have a sub-icon adjacent to the instructive text 103a that guides a user to interact with a physical button on the robotic arm to confirm the screw. Alternatively, the user may interact with the virtual button 103a via an input device, e.g., a touch screen or a mouse, to confirm the screw. When the user's input is received and/or considered to be valid, status change criteria may be met, and the first icon can automatically change to display different instruction and/or information to the user. As an example, the user can interact with the icon 103 to increase size of font for the currently level, L4-L, and/or size of a sub-icon, and such change by the user is updated to the icon 103 in real-time or near real-time.

In some embodiments, the status change criteria may be pre-determined by the user and determining whether the status change criterion is met is by a digital processing device e.g., using software or computer program. The determination can be after receiving electronic signal from the GUI, the robotic arm, the input device, or any other element in the robotic surgical system. For example, the digital processing device can determine whether a valid input from the user has been received or not. As another example, the status change criteria may include the robotic arm has reached a reference point relative to the anatomical structure or surgical tool. As yet another example, the status change criteria may be a vital sign change in the patient or any other change in the patient.

In some embodiments, the icon can include graphical information, such as a graphical sub-icon, text, color coding, or a combination thereof.

Figure 2:
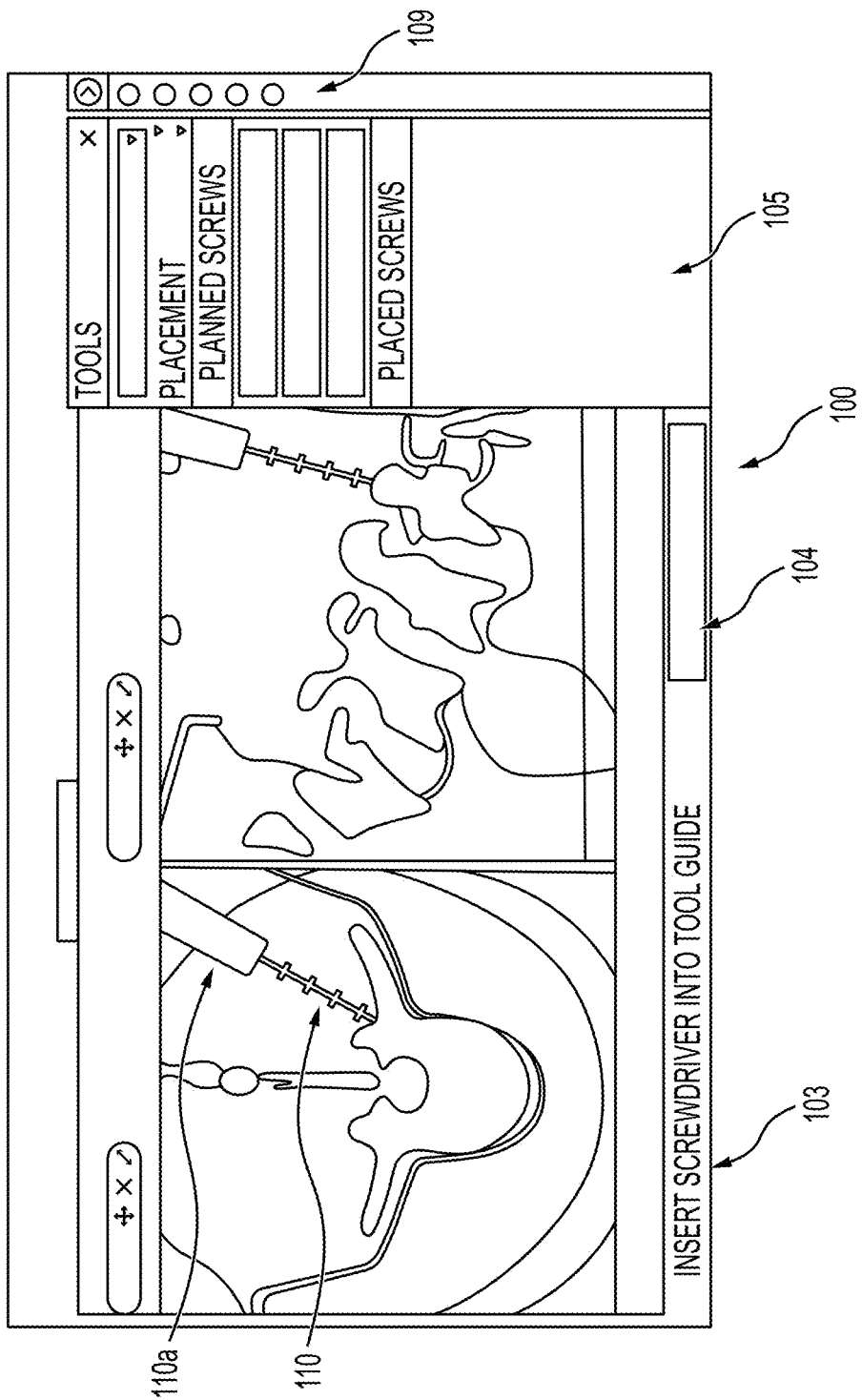
FIG. 2 shows an exemplary embodiment of the GUI herein; in this case, the representation of the screw driver, an active tool, is shown on the GUI but the representation of the corresponding screw is not shown on the GUI, in accordance with embodiments herein.

In some embodiments, the icon can customize presentation of information to the user depending on the user's interaction with it. For example, the icon can include a drop down menu as shown in FIG. 2. The icon can also include different graphical tabs 109 allowing a user to refine the content of the GUI.

In some embodiments, the icon 104 can include status information of the surgical procedure. For example, as shown in FIG. 1, different screws and/or trajectories, L5-L, L4-L, and L5-R are color coded differently to indicate which is/are planned for placement, and which have been placed, and which may haven't been planned yet. In some embodiments, the GUI also includes representation of the trajectories and their color coded status superimposed on the images. In this case, the trajectory being worked on 106, "L4-L", is shown in both images, and another trajectory that has been placed "L5-L" is shown in the second image 102. In some cases, the trajectory is an estimated or planned contour of the screw in the vertebra which guide the placement of the actual screw. In some embodiments, the "trajectory" may indicate the real trajectory associated with the surgical tool and extending from the tip of tool, e.g., the direction and distance a screwdriver may go into the vertebra. In some embodiments, the "trajectory" may indicate a planned trajectory that can be determined by the surgeon using a software, 106 or 107. In this embodiment, the presentation of the actual screw 108 is shown relative to the planned trajectory optionally for indication of the quality of screw placement. [Please review] [0040] In a different embodiment in FIG. 2, the icon 103 shows instructive information to the surgeon to insert screwdriver 110 into the tool guide 110a, another icon 104 shows screw L3-L is the screw that is actively being worked on, and yet another icon 105 shows robotic arm is being used, and there are three screws planned.

Instructive Information

In some embodiments, one or more icons disclosed herein include instructive information for the user. The instructive information can include size, location, name, type, or any other characteristics of a surgical tool. In some exemplary embodiments, the surgical tool can be a pedicle screw and/or a screwdriver. In some embodiments, the surgical tool can be a retractor assembly, a retractor blade, an implant, or any surgical tool that is used in the surgical procedure. The surgical tool can be a plurality of identical or different surgical tools at a same level of the spine or different locations of the spine.

In some embodiments, the instructive information includes direct instruction to the user, such instruction can be presented to the user in graphical form, in text, in audio, or any other forms that is perceivable by the surgeon. The instruction information can include a combination of elements disclosed herein. For example, it can include a phrase of direct visual or audio instruction, a color icon that blinks to draw the user's attention, and an audio cue that draws the user's attention if the user is not looking at the GUI.

In some embodiments, the instructive information can prompt the user to interact with one or more icons of the GUI directly. For example, the user may interact with the first icon 103 to switch the robotic arm between different modes. As shown in FIG. 2, the system is in a first mode that allows fine-tuning movement of the end effector while the robotic arm remains fixed in position, while in FIG. 17A; the system is in a second mode wherein the position of the robotic arm and end effector may be fixed and forces (e.g. skiving) experienced by the instrument in the end-effector or the end-effector itself are detected. Alternatively, or in combination, the instructive information can prompt the user to interact with an input device to enter an input that gets communicated to the robotic arm. For example, the user may be prompted by the instructive information to press a footswitch pedal to actuate the robotic arm.

The instructive information can change according to different stages of the surgical procedure. The instructive information can alter based on the status of the surgical tool, the robotic arm, the patient, or other part of the surgery. The instructive information can also be customized by a user. In some embodiments, the instructive information may be updated when there is an interaction with the GUI.

The update of the instructive information can be near real-time or real-time. In other words, no perceivable delay can be detected by the technician, surgeon, or otherwise user of the systems between the onset of an action causing the update and the actual update of the instructive information.

Status Information

In some embodiments, one or more icons 104 disclosed herein include status information for the user. The status information can be of the surgical procedure, the patient, and/or one or more surgical tools. In some embodiments, the status information may not be interactive with the user but is only updated by the surgical system when there is a change in the status. Such update of the status information or the instructive information can be near real-time or real-time. In other words, no perceivable delay can be detected by the technician, surgeon, or otherwise user of the systems.

In some embodiments, the status information can be presented to the user in graphical form, in text, in audio, or any other forms that is perceivable by the user. The status information can include a combination of elements disclosed herein. For example, it can include color-coded sub-icons representing trajectories where the color indicates whether the trajectory is active, complete, or not planned.

User Interaction

In some embodiments, the user interacts with the GUI directly via a first input device. In some cases, the first input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input.

In some embodiments, the user provides an input at the first input device or at a second input device. In some cases, the input is not directly provided at the GUI but at another actuation element, for example, a footswitch pedal that communicates with the surgical system or the robotic arm to actuate the robotic arm.

In some case, the user interaction can be a combination of direct interaction with the GUI and indirect interactions. In some embodiments, the user interaction is a transient action, e.g., flipping a switch. In other embodiments, the user interaction can be a continuous action, e.g., continuously pressing and holding down the foot pedal.

Robotic Arms

Disclosed herein are robotic arms 2211. The robotic arms are in communication with a digital processing device 2001 of the robotic surgical system, so that the surgeon can interact with the robot using the GUI 100, and the user interaction can be transmitted from the digital processing device to the robotic arm(s). In some cases, the robotic arm is also in communication with other hardware, such as an input device that is part of the digital processing device or external to the digital processing. An example of such hardware is a foot pedal or a handle.

The robotic arm 211 can work automatically without the control of a user during at least part of a surgical procedure. For example, the robotic arm can automatically approach the surgical site until a stopping criterion has been detected. The stopping criterion can be pre-determined by the user, and the digital processing device 2001 can determine whether the stopping criterion is met or not. For example, the robotic arm may use its sensor to sense the tracking array or patient array, the digital processing device determines the distance to the array, and see if the robotic arm needs to stop or not.

The robotic arm can work semi-automatically with various level of control by the user or surgeon. The user may control the movement of the robotic arm with a foot pedal, a motion clutch button, a confirmation button, or a combination thereof. Alternatively or in combination, the user may also grab a control handle toward the distal end of the robotic arm and hand-guide its motion. As an example, the robotic arm can move within a pre-determined range with the surgeon's control or move by the surgeon but eliminate certain errors in the surgeon's motion, e.g., hand shaking.

The robotic arm can include a distal end 2216 that can actively grab a surgical tool or hold a surgical tool securely and reversibly via a coupling. The robotic arm may include one more image capturing device at or near the distal end of the robotic arm to ensure accurate movement of the robotic arm relative to the anatomical structure of the patient. In some embodiments, the robotic arm may include another digital processing device 2001 of its own so that it may execute software or computer program using the digital processing device of its own.

In some cases, the robotic arm can work under different modes. Switching among different modes can be done automatically, optionally depending on the stage of the surgical procedure. Alternatively, switching among different modes can be done manually by the user at the GUI. In one exemplary mode, the robotic arm can move with predetermined parameters, direction, speed, acceleration, etc. until a stopping criterion is met. In another exemplary mode, the robotic arm can only move in a determined range, e.g., only rotation at the distal tip in the range of −10 to 10 degrees.

Figure 22:
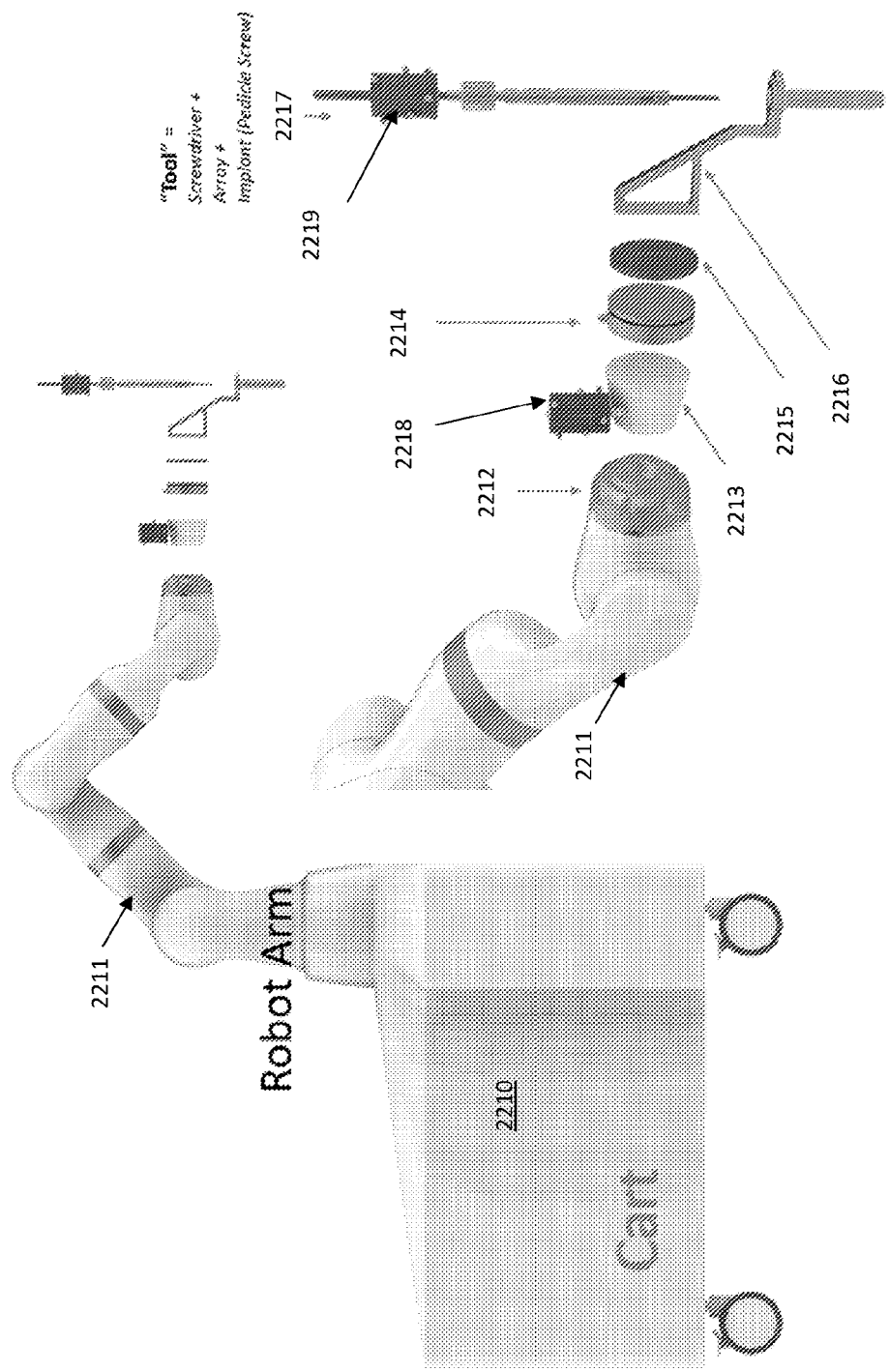
FIG. 22 shows an exemplary embodiment of the robot or robotic arm disclosed herein.

In some embodiments, the robotic arm includes one or more sensors configured to sense parameters can be used for skive detection. Such sensors may be located at or near the distal end of the robotic arm. Sensors may also be located anywhere at the robotic arms. Such sensor can include a force sensor, a torque sensor, a strain sensor, a pressure sensor, a resistance sensor, or any other type of sensor. In an exemplary embodiment as shown in FIG. 22, the force and/or torque sensor 2214 is attached to the distal end of the robotic arm 2211 and in connection with the tool guide 2216 and tool assembly 2217. The connection may be via a mechanical or magnetic connector 2215. In some embodiments, the sensor includes one or more strain gauges.

In some embodiments, the skive detection step or process utilizes information provided by the sensor, e.g., force/torque sensor, alone or in combination, with information associated with robotic arm movement that can be made available using other elements of the robotic surgical system. Such information may include speed, acceleration, impedance to moving the robotic arm, etc. In some embodiments, the force/torque sensor can generate force/torque information in a three-dimensional coordinate system. By 3D registration of the 3D coordinate system of the sensor to the 3D coordinate system to the patient, we can generate directional force/torque information. For example, a measured force can be transformed into superior, inferior, lateral, or medial forces when it is in the patient's coordinate system. If the force/torque is above a pre-determined threshold in one or more pre-selected directions, then, the robotic surgical system may generate a visual, audio, or otherwise a form of warning to the user. The force measured herein may include sheer against an anatomical feature such as vertebra or soft tissue.

In some embodiments, the robotic arm 2211 and/or the digital processing device 2001 herein can detect a change in its speed, acceleration, and/or position. For example, if the tool slips away from a desired surgical spot, such sudden or abrupt change in speed, acceleration, and/or position can be used as an indicator of possible skive, and a warning signal can be send to the surgeon upon detection of such changes.

Using the Robotic Surgical Systems

In some embodiments, disclosed herein is a method for using the robotic surgical system 2101. The method may include one or more method steps or operations disclosed herein but not necessarily in the order that the steps or operations are disclosed herein.

One or more method steps or operations disclosed herein can be performed in real-time or near real-time so that it advantageous facilitate continuous interaction between the user and the robotic arm of the surgical procedure.

FIGS. 2-19 show exemplary embodiments of the GUIs 100 at different stages or steps of a surgical procedure using the robotic surgical system.

FIG. 2, in one embodiment, shows the axial trajectory CT image 101 on the left and the sagittal trajectory CT image 102 on the right. Both images include an overlay of the active tool 110, in this case, a screwdriver working on L3-L screw placement. The active tool can be color coded. The active tool can also be at its full dimension, so do the anatomical structures. The drop down menu 109 also reflects the screw that is being worked on. In this particular case, the trajectory of the screw, e.g., element 106 in FIG. 1, is not visible in any of the images shown in the GUI, however, it can be necessary to see the planned trajectory inside the pedicle when the screwdriver is the active tool and/or placement of the screw is in progress.

Figure 3:
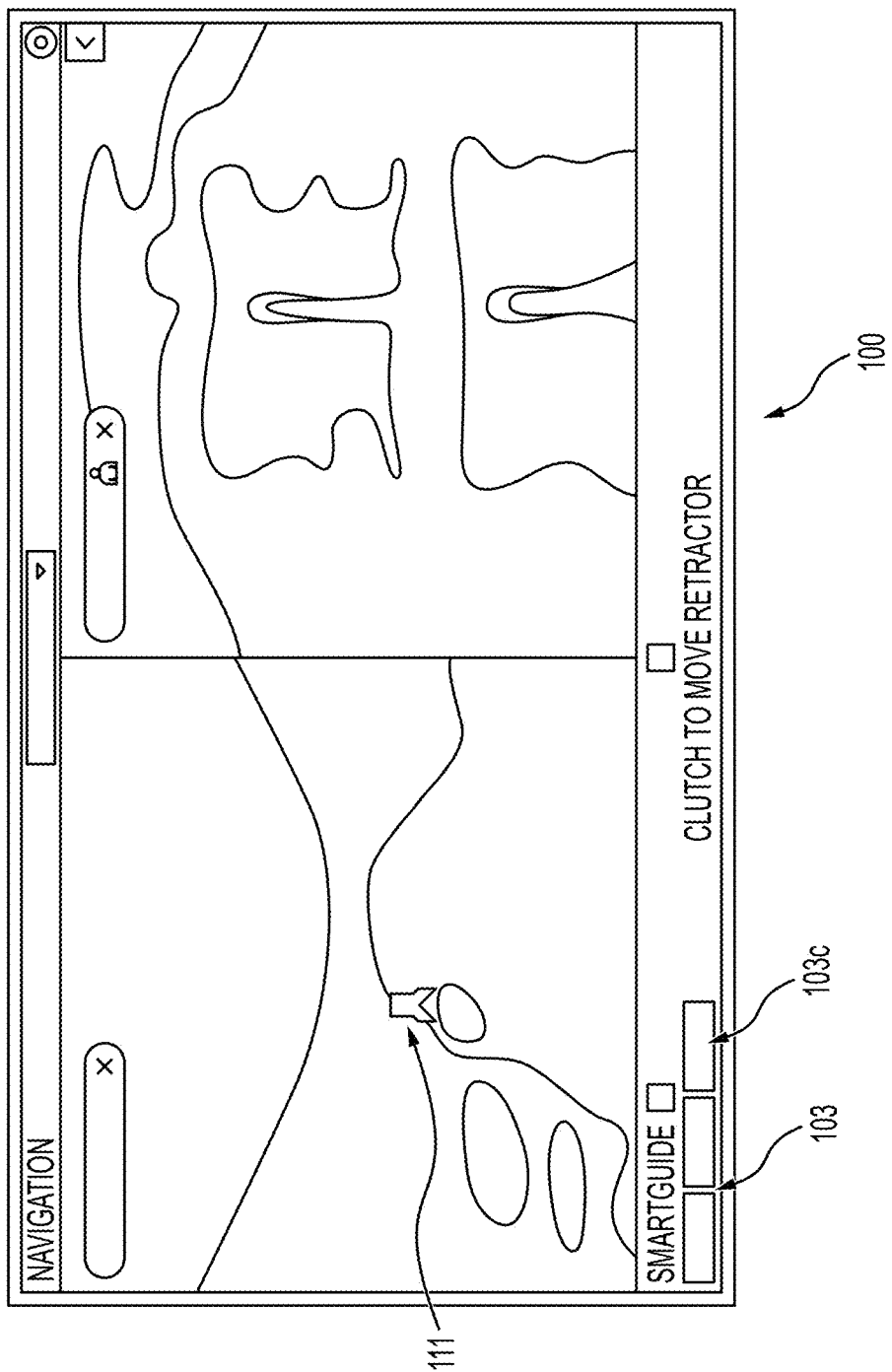
FIG. 3A and FIG. 3B show an exemplary embodiment of the GUI herein; in this case, instructive information for a user to interact with the robotic arm and start an operation of the surgical tool in a lateral interbody fusion procedure, in accordance with embodiments herein.

FIG. 3, in another embodiment, shows a step associated with operation of a surgical retractor, e.g., in the extreme lateral interbody fusion (XLIF) procedure. In this embodiments, the lateral (left) and coronal or AP view (right) of the patient are shown side by side using the GUI 100. Superimposed on the image(s) is graphical representation of the posterior retractor blade 111. The representation of the blade 111 moves in accordance with the actual blade movement by the robotic arm, in near real-time or real-time.

One or more steps can be performed so that no perceivable delay can be detected by the technician, surgeon, or otherwise user of the systems. One or more steps can be performed so that no perceivable delay exist in performing the medical procedure.

In some embodiments, real-time or near real-time performance or update disclosed herein include a very small delay of less than 1 second, 0.8 seconds, 0.6 seconds, 0.5 seconds, 0.4 seconds, 0.3 seconds, 0.2 seconds, 0.1 seconds, 0.08 seconds, 0.06 seconds, 0.05 seconds, 0.02 seconds, or 0.01 seconds. In some embodiments, real-time performance disclosed herein includes a very small delay of less than about 1 second, 0.8 seconds, 0.6 seconds, 0.5 seconds, 0.4 seconds, 0.3 seconds, 0.2 seconds, 0.1 seconds, 0.08 seconds, 0.06 seconds, 0.05 seconds, 0.02 seconds, or 0.01 seconds. The time delay herein can be the time duration from the onset of a step to the end of the same step, or any subsequent step(s). The time delay herein can be the time duration from the onset of an update or change to the end of the same update or change in the GUI, or any subsequent update(s) or change(s) in the GUI. As an example, the user can follow the instruction to depress and hold motion clutch button at the GUI. This, together with other user input, or alone, may trigger the robotic arm to enter "fine movement" mode as shown at the status indicator bar. The time delay to enter and display "fine movement" mode after receiving the user's input at the input device is not perceivable by the user.

Continuing to refer to FIG. 2, in this embodiment, the robotic arm at the beginning of this step, may be directly lateral with the tool holder connected to the XLIF retractor. The first icon shows instructive information to the user to clutch the robotic arm to the retractor in order to move the retractor. The user can follow the instruction to depress and hold motion clutch button at the GUI or otherwise a button in the robotic surgical system. This, together with other user input, or alone, may trigger the robotic arm to enter "fine movement" mode as shown at the first icon 103 of the status indicator bar. The time delay to enter "fine movement" mode after receiving the user's input is not perceivable by the user. The range of motion for the robotic arm in the fine movement mode can be predetermined by a user or surgeon. For example, the robotic arm movement range can be restricted to a cone of about +/−4 mm and about +/−10 degrees. An audio cue may be provided to the user, e.g., repetitive beep, while motion clutch is depressed, and single bong when motion clutch button is released. The user can depress the button corresponding to the sub-icon 103b on the robotic arm to start the motion of the robotic arm. Alternatively, the user can interact directly with one or more sub-icons 103b on the GUI, e.g., "translate," "tilt," "insertion," to control the type of motion of the robotic arm.

FIGS. 4-19 show different steps or stages in an exemplary embodiment of multiple pedicle screw placements using the robotic surgical system disclosed herein.

Figure 4:
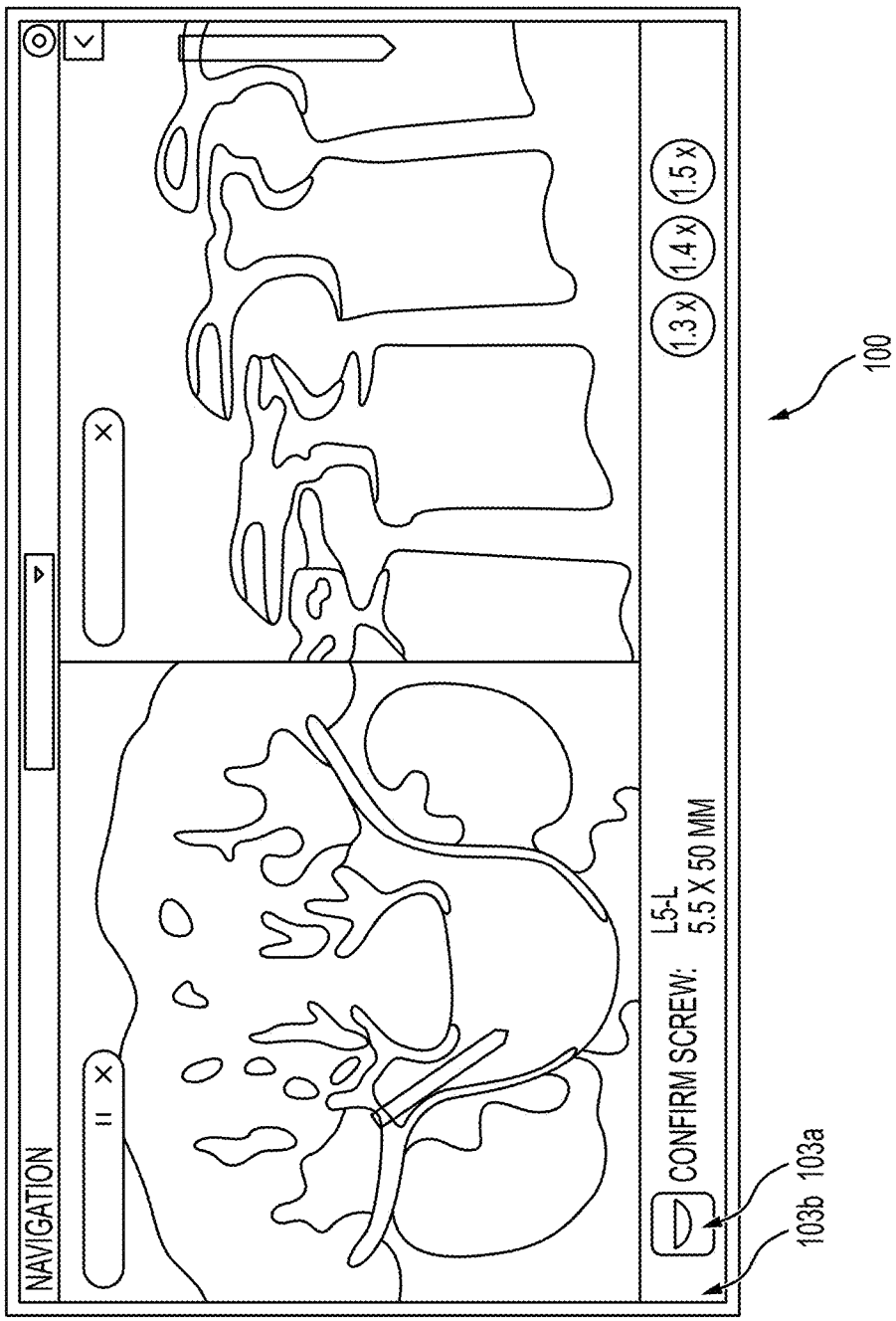
FIGS. 4-19 show exemplary embodiments of the GUI herein; in this case, at exemplary stages in the operation of pedicle screw placement, in accordance with embodiments herein.

One step in the pedicle screw placement procedure is to select a level of the vertebra for the next screw placement. Referring to FIG. 4, L5-L, is the current level being selected for placement and highlighted with the specific color coding. Two other levels are planned for screw placement, and are shown together with L5-L in the status indicator bar with a different color indicating a different status. With presentation of the instructive information "confirm screw: L5-L" to the user, the user can depress the button on the robotic arm that corresponds to the virtual button 103a to select L5-L as the first planned screw so that it will be placed first. An audio cue may be provided upon the button press. The screw confirmation may include confirmation of one or more of: level/location for screw placement, screw size, and type. The robotic arm at this step may be directly lateral to the patient if the patient is in lateral decubitus position. There can also be a LED color ring at the robotic arm, the LED color ring may display a static green color when the robotic is not in motion and blinking green otherwise. The GUI may provide a corresponding icon or sub-icon that indicate the status of the LED ring on the robotic arm. For instance, the corresponding icon may blink the same color as the LED ring.

Figure 5:
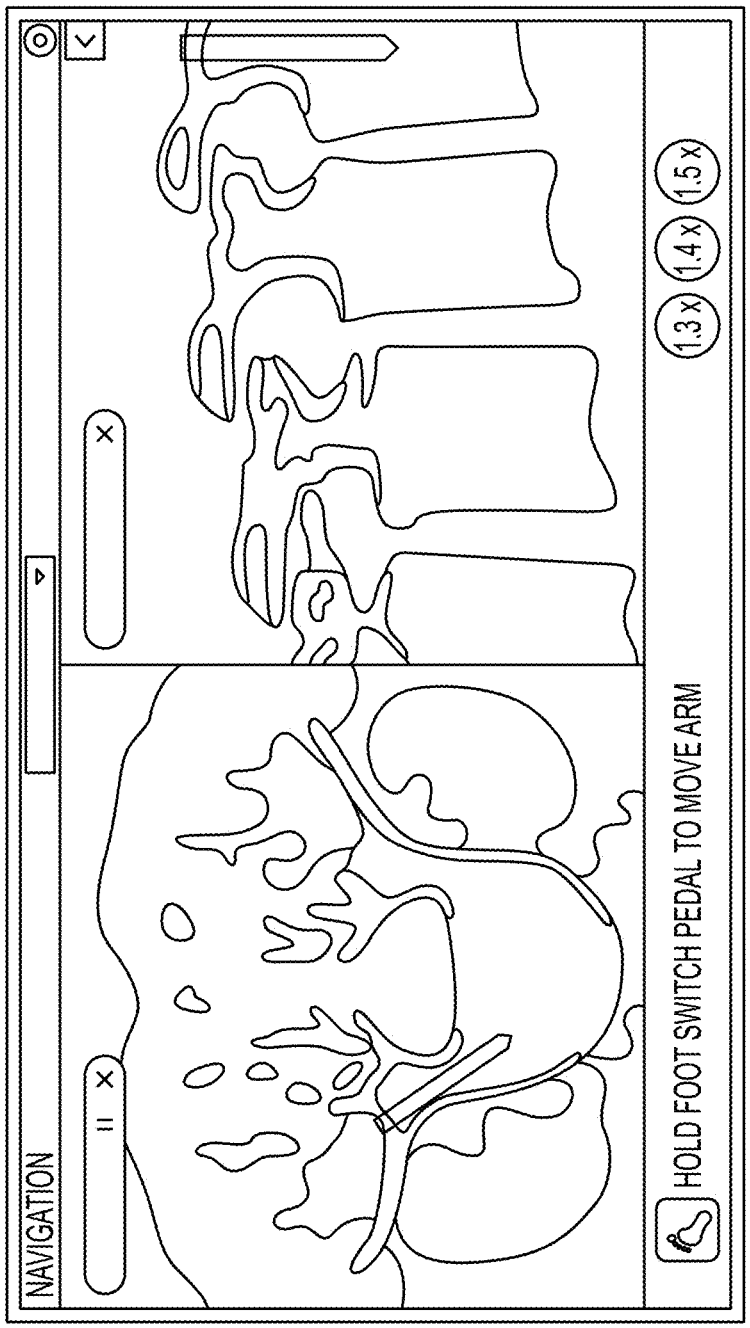

Referring to FIG. 5, in an exemplary embodiment, another step in the pedicle screw placement procedure is to approach the planned trajectory of the screw using the robotic arm. This step can be subsequent to the step in FIG. 4. The instructive information in the first icon has been updated to instruct the surgeon to "hold foot pedal to move robotic arm." The user can respond to the instructive information by providing a user input, e.g., depression and holding of the foot pedal to actuate automatic motion of the robotic arm to approach planned trajectory stop when distal aspect the robotic arm, e.g., tool holder, reaches level of patient reference array. The GUI can also provide a visual cue by blinking green at the LED color ring on the robotic arm. Another visual cue that can be provided at the GUI is graphical representation of robotic tool guide in both the axial and sagittal DRR images. The visual cue are changing in real-time and near real-time with robotic arm's relative position to the anatomical structure. The representation of the tool guide can be about 1 cm above the level of the pedicle in this step. Simultaneously, the first image and the second image are also updated in real-time or near real-time with the motion of the robotic arm to best assist visualization of the planned trajectory, the tool guide, the actual trajectory relative to the anatomy of the patient.

Figure 6:
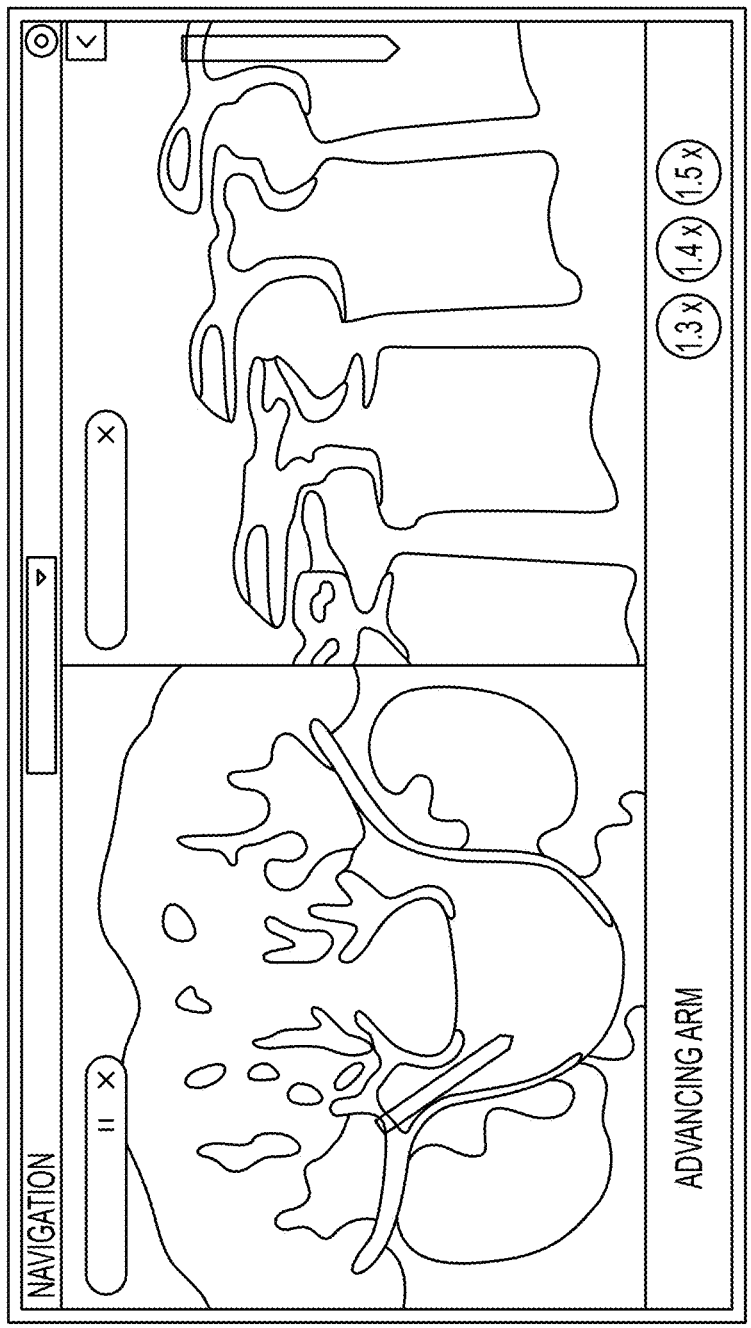

Referring to FIG. 6, in an exemplary embodiment, another step in the pedicle screw placement procedure is robotic arm movement to reach the pedicle. This step can be subsequent to the step in FIG. 5. The instructive information in the first icon can be updated to instruct the surgeon to advance the robotic arm. At this step, the user's input can be depressing and holding motion clutch button on the robotic arm in order to advance the robotic arm. The robotic arm may automatically move toward the patient until reaching the pedicle level. In this particular embodiment, the robot automatically takes linear motion towards the patient until graphical representation of the robotic tool guide reaches level of the pedicle. The LED color ring on the robotic arm can blink green while the robot is in motion and a static green color when the robotic is not in motion. An audio cue may be provided by the GUI to the user, e.g., repetitive beep, while the footswitch or motion button is depressed, and single bong when motion is complete. At this step, graphical representation of robot tool guide may be in both images and at the level of the pedicle.

Figure 7:
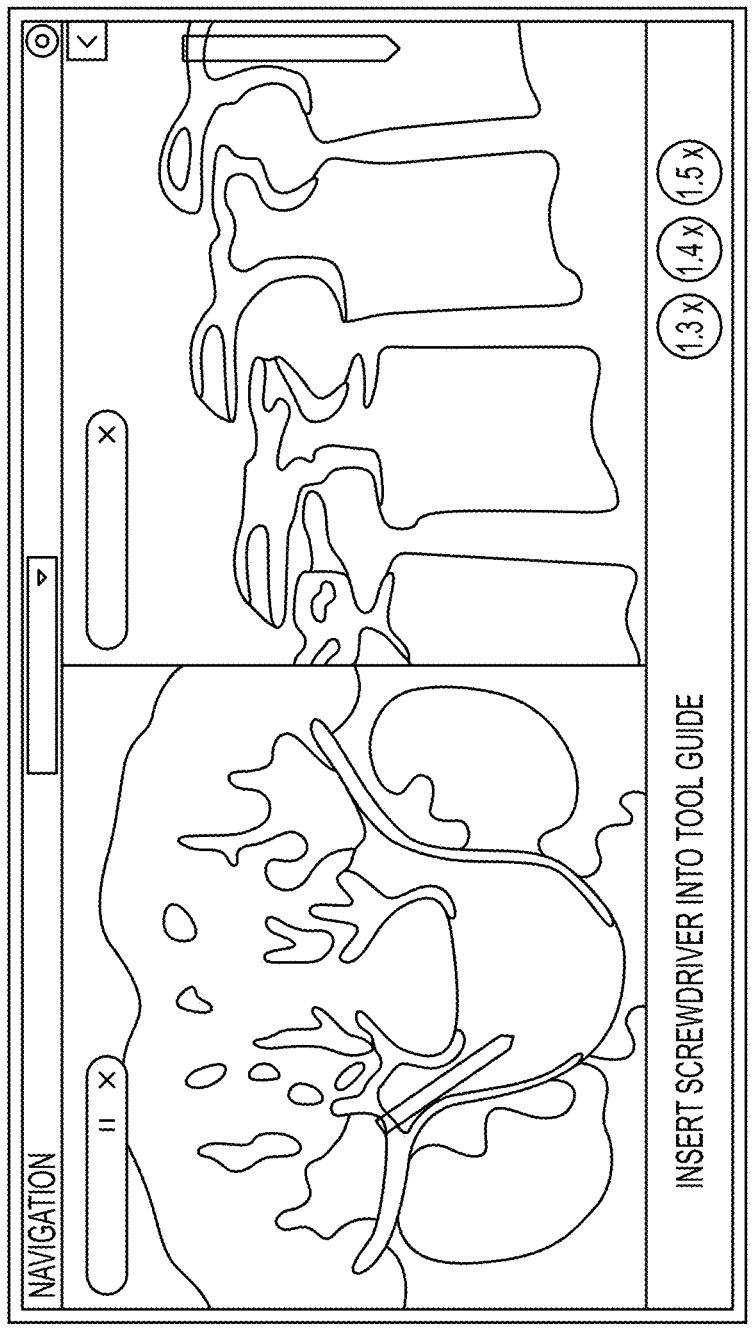

Referring to FIG. 7, in an exemplary embodiment, another step in the pedicle screw placement procedure is robotic arm position hold. This step can be subsequent to the step motion to approach step in FIG. 6. The instructive information in the first icon has been updated to instruct the surgeon to insert screwdriver 110 into the tool guide 111. At this step, the robotic arm is in a hold or locked position. At this step, the user's input can be inserting the screwdriver into tool holder without assistance from the robotic arm. At this step, graphical representation of robot tool guide may disappear and the representation of screwdriver may appear in both images. The change in graphical representation at the GUI can occur in real-time or near real-time.

Figure 8:
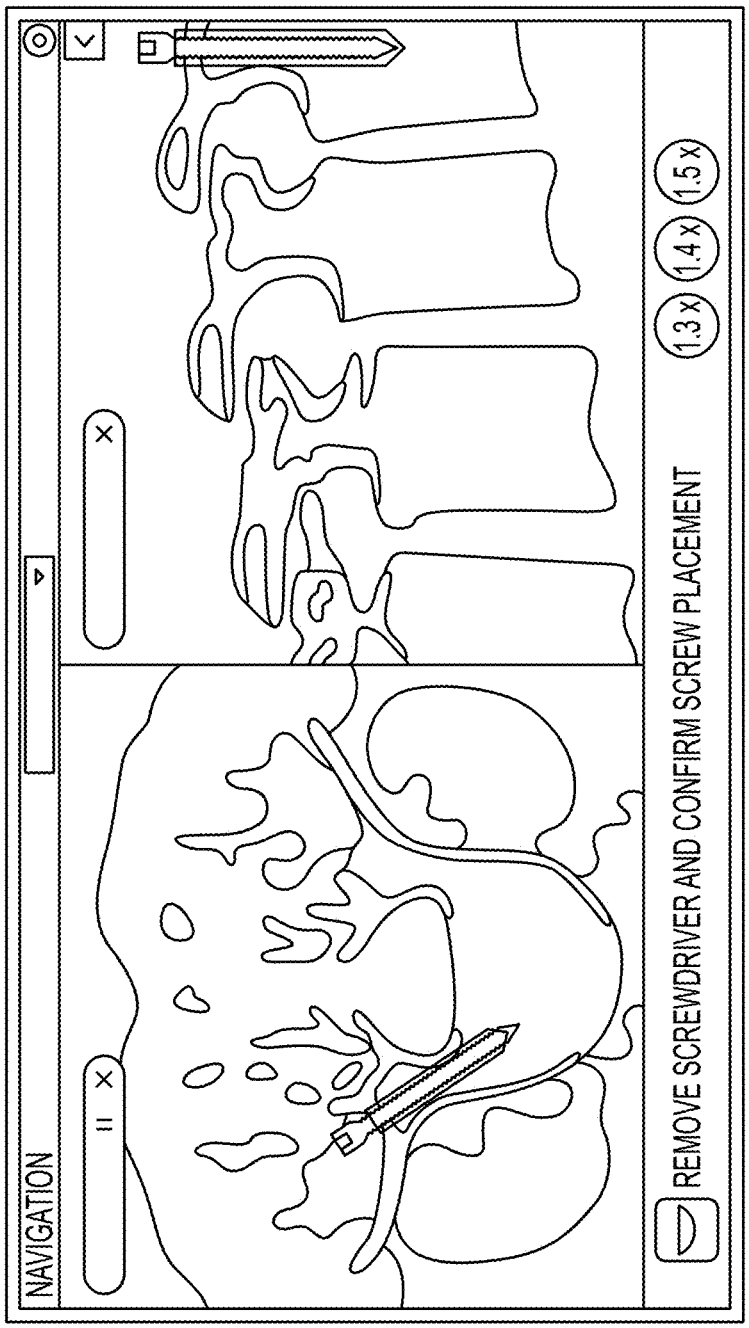

Referring to FIG. 8, in an exemplary embodiment, another step in the pedicle screw placement procedure is screw placement. This step can be subsequent to the step in FIG. 7. The instructive information in the first icon has been updated to instruct the surgeon to remove screwdriver 111 and confirm screw placement. At this step, the user's input can be manual removal of the screwdriver after screw placement from the tool guide and depressing a button on the robotic arm to confirm screw placement. An audio cue may be provided by the GUI to the user, e.g., bong, when motion is complete. At this step, graphical representation of the screw driver may disappear and the representation of robot tool guide may appear in both images.

Figure 9:
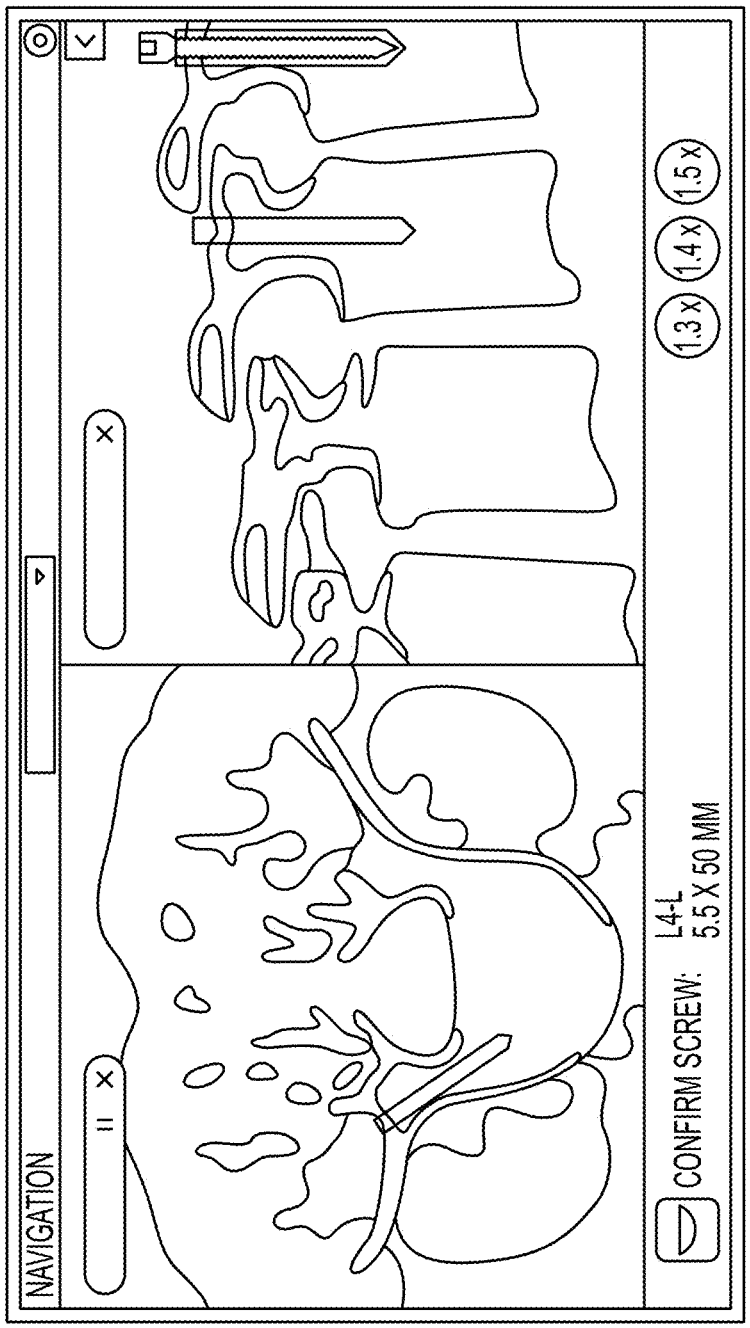

Referring to FIG. 9, in an exemplary embodiment, another step in the pedicle screw placement procedure is ready for the next pedicle. This step can be subsequent to the step in FIG. 8. The status information has been updated to shown now L5-L screw placement is complete, e.g., color changed to green, and now the screw being worked on is L4-L, e.g., color changed to purple. The superimposed representation of the trajectory has also been updated to shown the placed screw 107, 108 in the tool guide with a different color than the tool guide with the screw being planned 106. As the first image has been updated to move to L4 from L5 vertebra, the placed screw is not visible in the axial DRR at this step. L4-L, is the current level being selected for placement and highlighted with the specific color coding. One other level is planned, and shown together with the L5-L and L4-L in the status indicator bar with a different color to indicate a different status. This level can be selected by the user, after presentation of the instructive information "confirm screw: L4-L" to the user, by interacting with a button on the robotic arm, in particular, the user can depress the button to select L4-L as the next screw to be placed. An audio cue may be provided upon the button depression. The robotic arm at this step may be located directly lateral to the patient if the patient is in lateral decubitus position with no motion required. The LED color ring may display a static green color. The GUI may also provide an audio cue to the user upon depressing the button for confirming the screw.

Figure 10:
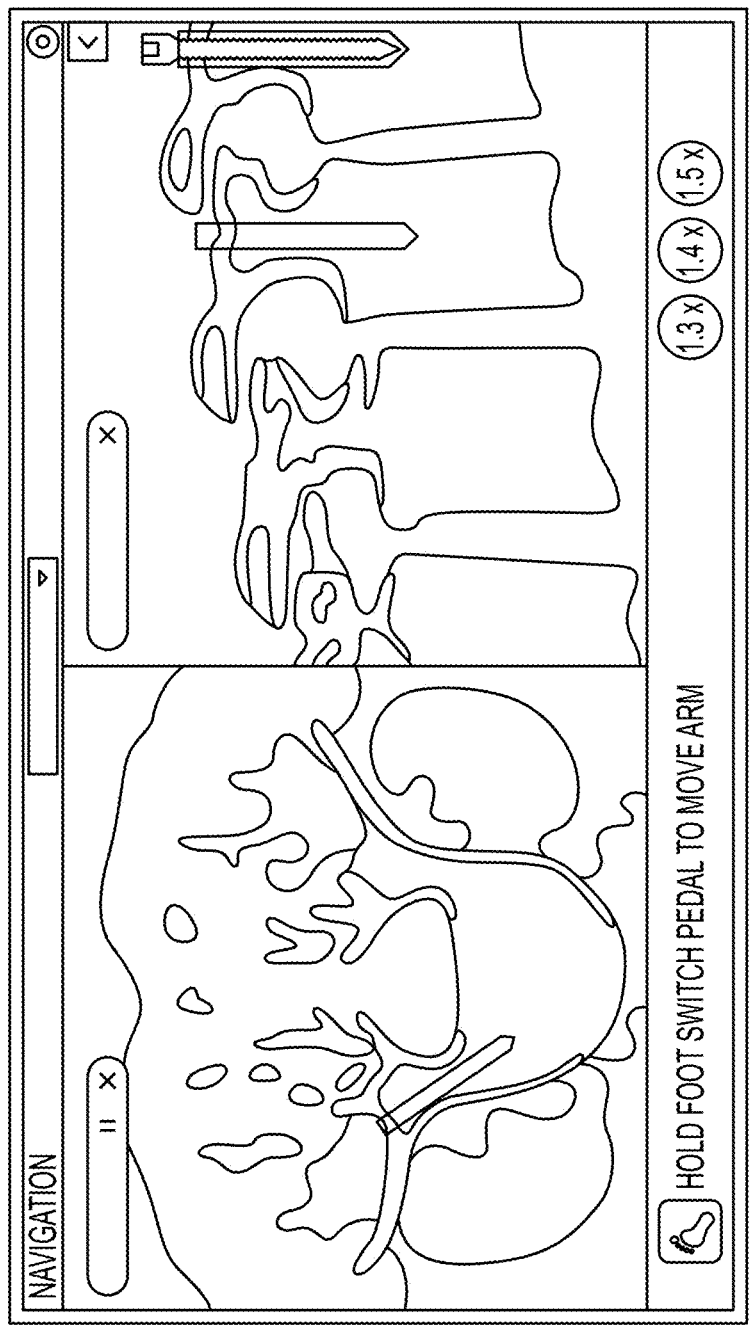

Referring to FIG. 10, in an exemplary embodiment, another step in the pedicle screw placement procedure is to approach the planned trajectory of the screw using the robotic arm. This step can be subsequent to the step in FIG. 9. The instructive information in the first icon has been updated to instruct the surgeon to "hold foot switch pedal to move robotic arm." The user can respond to the instructive information by providing a user input, e.g., depression and holding of the foot pedal to actuate automatic motion of the robotic arm to planned trajectory stopping when distal aspect the robotic arm, e.g., tool holder, reaches level of patient reference array. The GUI can also provide a visual cue by blinking green at the LED color ring. Another visual cue that can be provided at the GUI is graphical representation of robotic tool guide in both the axial and sagittal DRR images. The representation of the tool guide can be about 1 cm above the level of the pedicle in this step.

Figure 11:
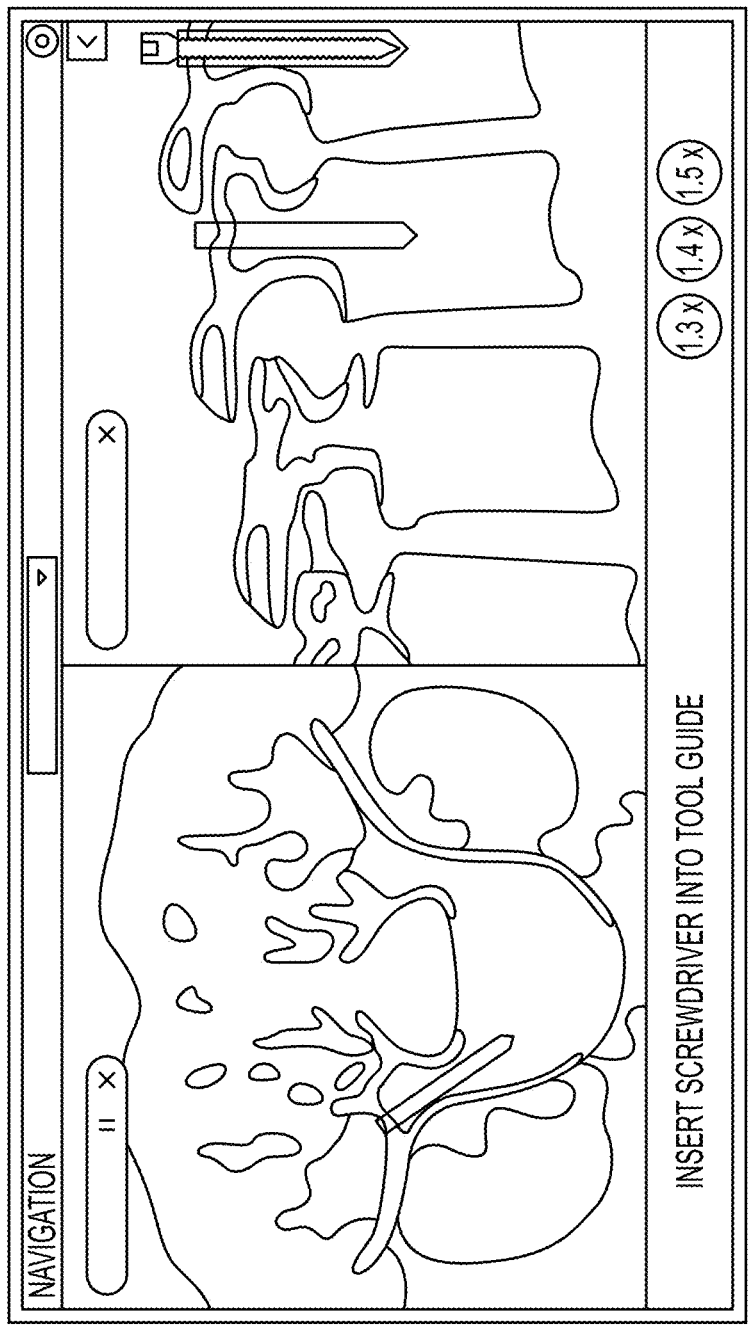

Referring to FIG. 11, in an exemplary embodiment, another step in the pedicle screw placement procedure is robotic arm movement in fine movement mode to reach the pedicle. This step can be subsequent to the step in FIG. 10. The instructive information in the first icon has been updated to instruct the surgeon to insert screwdriver into the tool guide shown in both images. At this step, the user's input can be inserting the screwdriver into tool holder without assistance from the robotic arm. An audio cue may be provided by the GUI to the user, e.g., repetitive beep, while the foot pedal is depressed, and single bong when motion is complete. At this step, graphical representation of robot tool guide may disappear and the representation of screwdriver may appear in both images.

Figure 12:
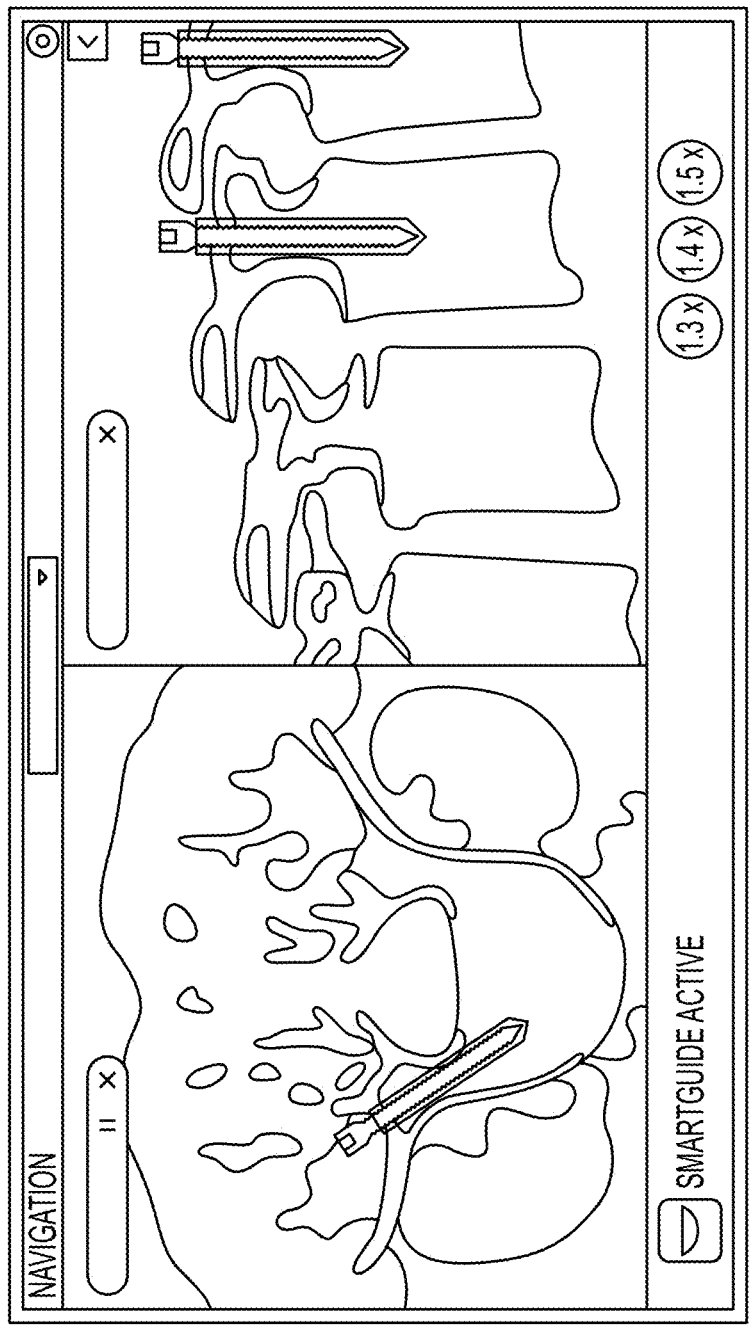

Referring to FIG. 12, in an exemplary embodiment, another step in the pedicle screw placement procedure is robotic arm movement in fine movement mode to reach the pedicle. This step can be subsequent to the step in FIG. 11. The instructive information in the first icon has been updated to the Smart Guide mode is active and may also instruct the surgeon to insert screwdriver into the robot tool guide. At this step, the user's input can be depressing and holding a button on the robotic arm to enter fine movement mode and/or actuate the robotic arm in fine movement mode. In some embodiments, in the Smart Guide mode, the robotic arm moves under the control of the surgeon, in other words the surgeon can hand-guide the robotic arm for at least a portion of the robotic arm's movement. Alternatively, the robotic arm moves automatically. In this fine movement mode, the robotic arm is restricted to move in a predetermine range, e.g., in a cone of about +1–4 mm and/or about +/−10 degrees. The LED color ring can blink green while the robot is in motion and a static green color when the robotic is not in motion. A first audio cue may be provided by the GUI to the user, e.g., repetitive beep, while motion clutch is depressed, and a second audio cue, e.g., bong, when motion is complete. At this step, graphical representation of robot tool guide dynamically moves as user manipulates the control handle or motion clutch button.

FIGS. 13-16 and 18 show steps in the pedicle screw placement procedure similar to FIGS. 8-11, except in addition to the representation of the current active screw placement information, there can also be representation of the screw and the robot tool guide for a screw that has been placed. The status indicator bar can also reflect the difference in the status information.

Figure 17B:
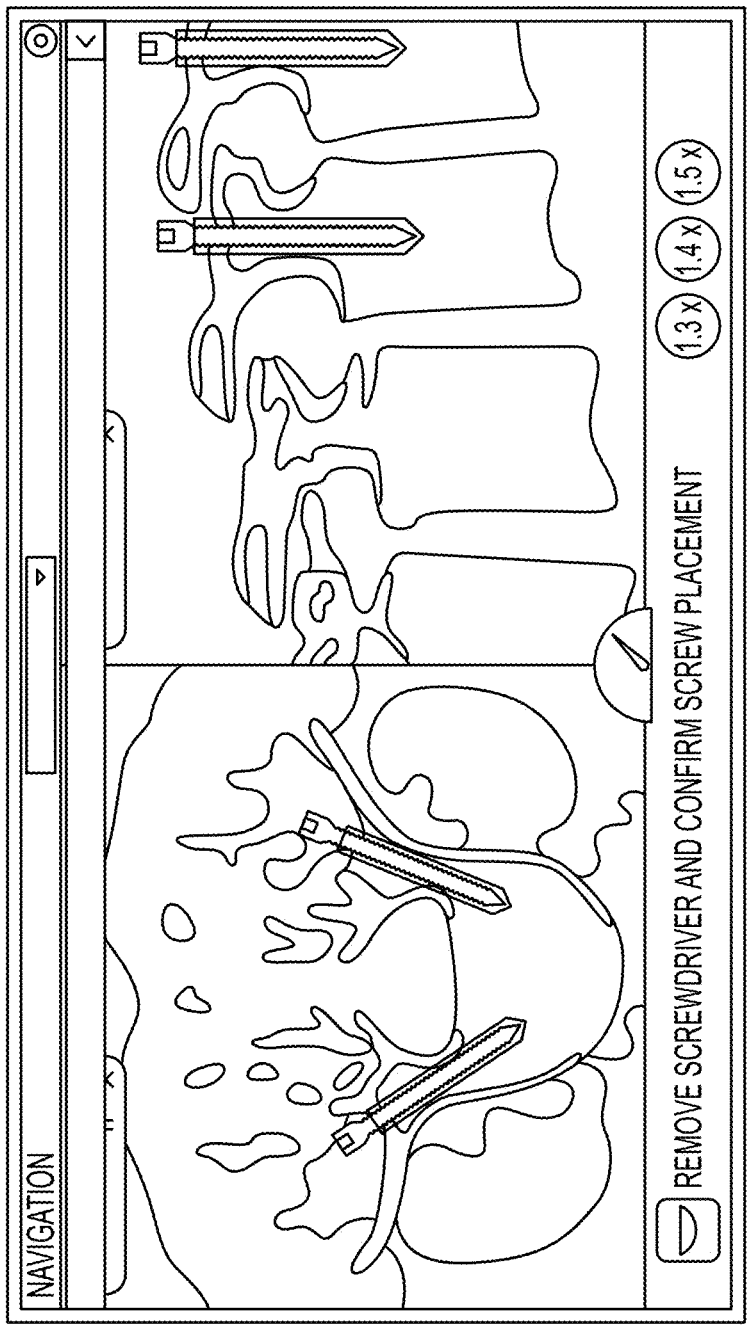
Figure 17A:
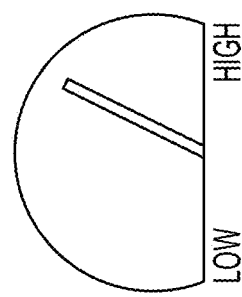

FIG. 17A in an exemplary embodiment, shows a force detection mode for the robotic arm. The force detection mode can be automatically triggered when there is any predetermined signal detected at the sensor at the robotic arm, for example, when there is a force on the tool guide. In this particular embodiment, the GUI instructs the surgeon to remove screwdriver and confirm screw placement at the status indicator bar. A graphical representation of the force detection meter as shown in FIG. 17B is overlaid with the images to indicate the relative skive level or alternatively, a quantitative parameter related to the skive, e.g., force. The user input can be sheer force applied manually to the screw. The LED color ring may blink a color different than other steps in the procedure, e.g., yellow. Such skive detection may facilitate user's interaction, e.g., placement of screw, by providing directional information of the movement of the screw.

Figure 19:
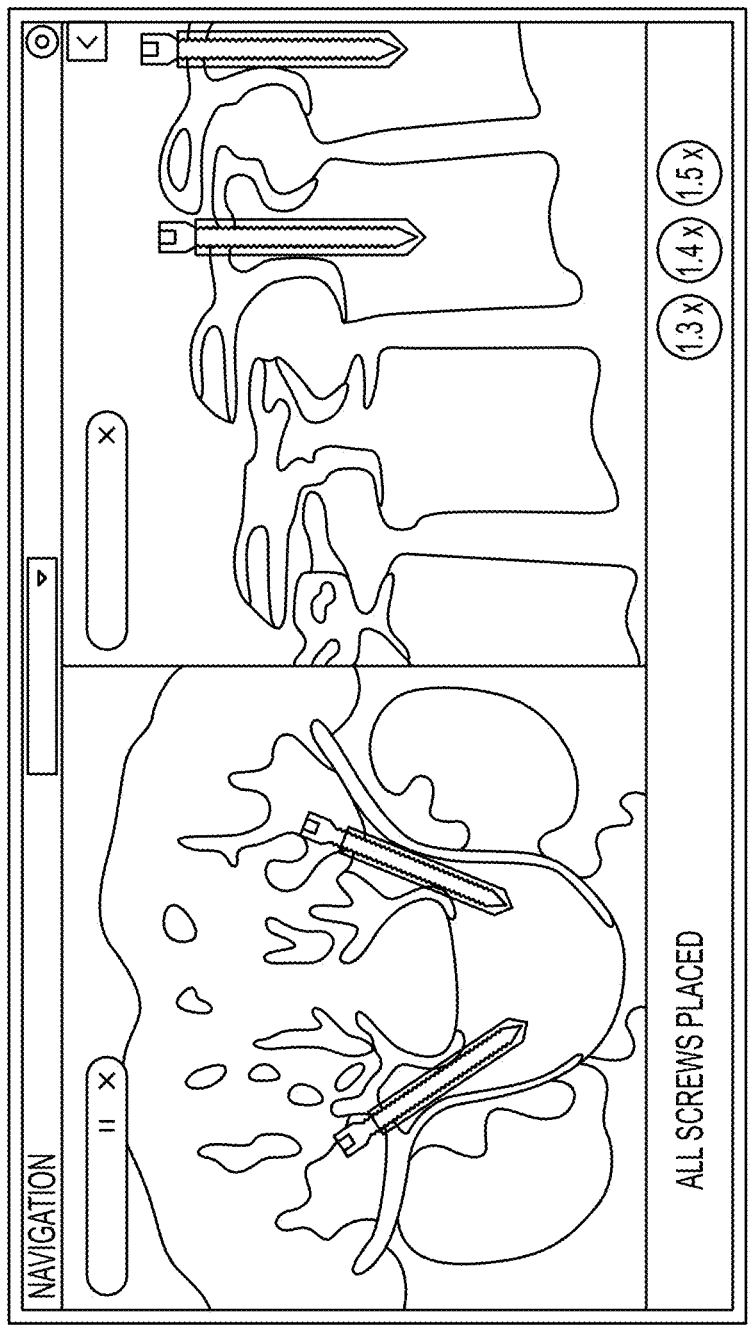

FIG. 19 shows the end step of the pedicle screw placement procedure with representation of the screws placed within the robotic tool guide. The status indicator bar updated to indicate complete placement of all three screw.

Figure 21:
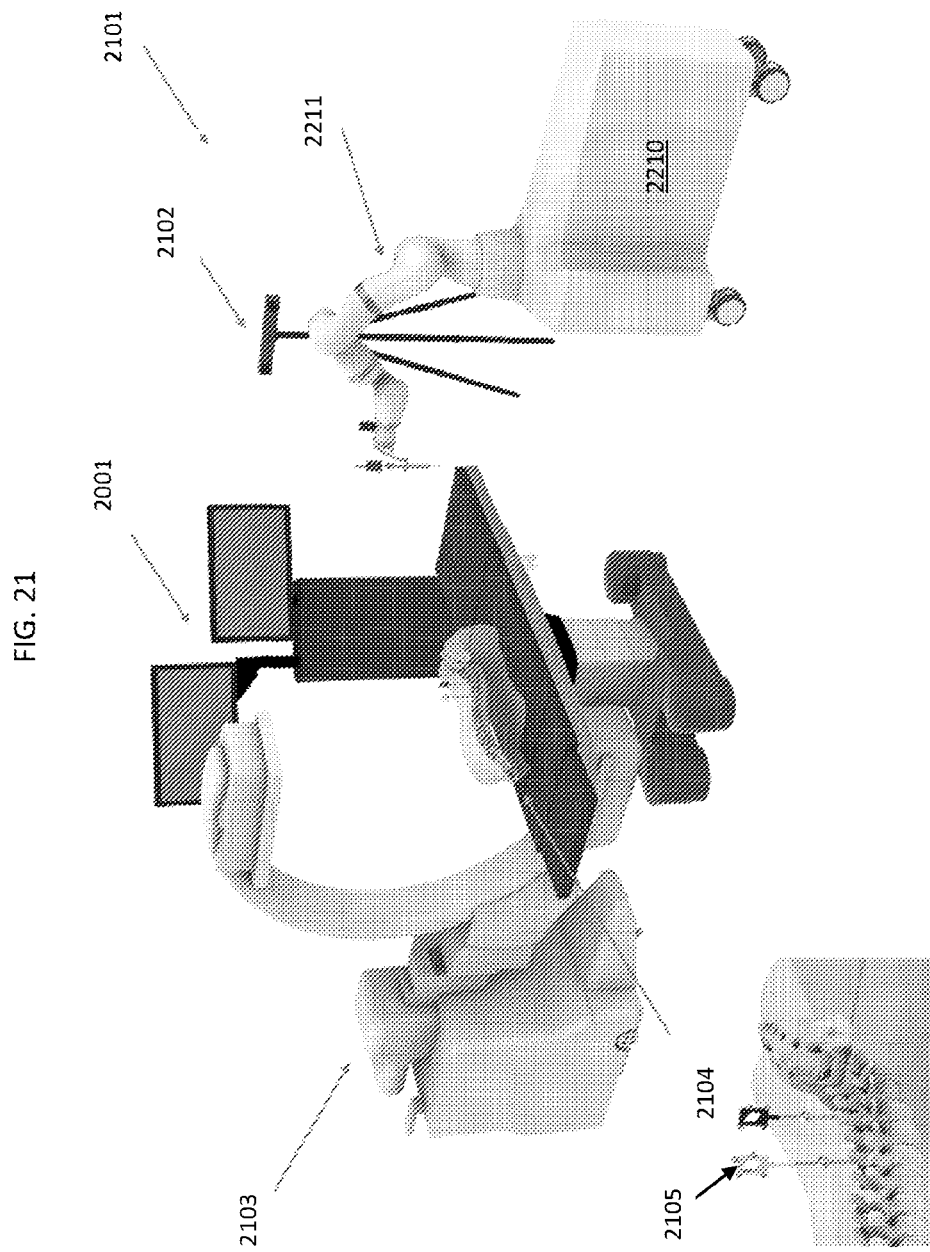
FIG. 21 shows an exemplary embodiment of the robotic surgical system disclosed herein.

FIG. 21 shows an exemplary embodiment of the robotic surgical system herein. The robotic surgical system 2101 may include a cart 2210 and a robotic arm 2211 as disclosed herein. The system 2101 may also include an imaging device, e.g., a camera 2102, a digital processing device 2001 as disclosed herein, a medical imaging device 2103, e.g., C-arm. The system 2101 may be used to facilitate any medical or surgical procedure on a spine 2104. Various tracking arrays 2105 for tracking surgical instruments and/or the patient can also be used with the robotic surgical system.

FIG. 22 shows an exemplary embodiment of the robotic arm 2211 disclosed herein. The robotic arm 2211 may include a medial flange 2212 at its distal portion. The medial flange can be coupled to an adapter that is coupled with a tracking array 2213. Such adapter may enable coupling to a sensor 2214. The sensor 2214 may be fixedly attached or removablely attached to the adapter. The sensor is connected with a tool guide connector 2215 which is configured to allow quick and reversible connection to a tool guide 2216. The tool guide is at the distal end of the robotic arm, and it is for securing holding one or more surgical tools 2217 thereon.

Figure 23:
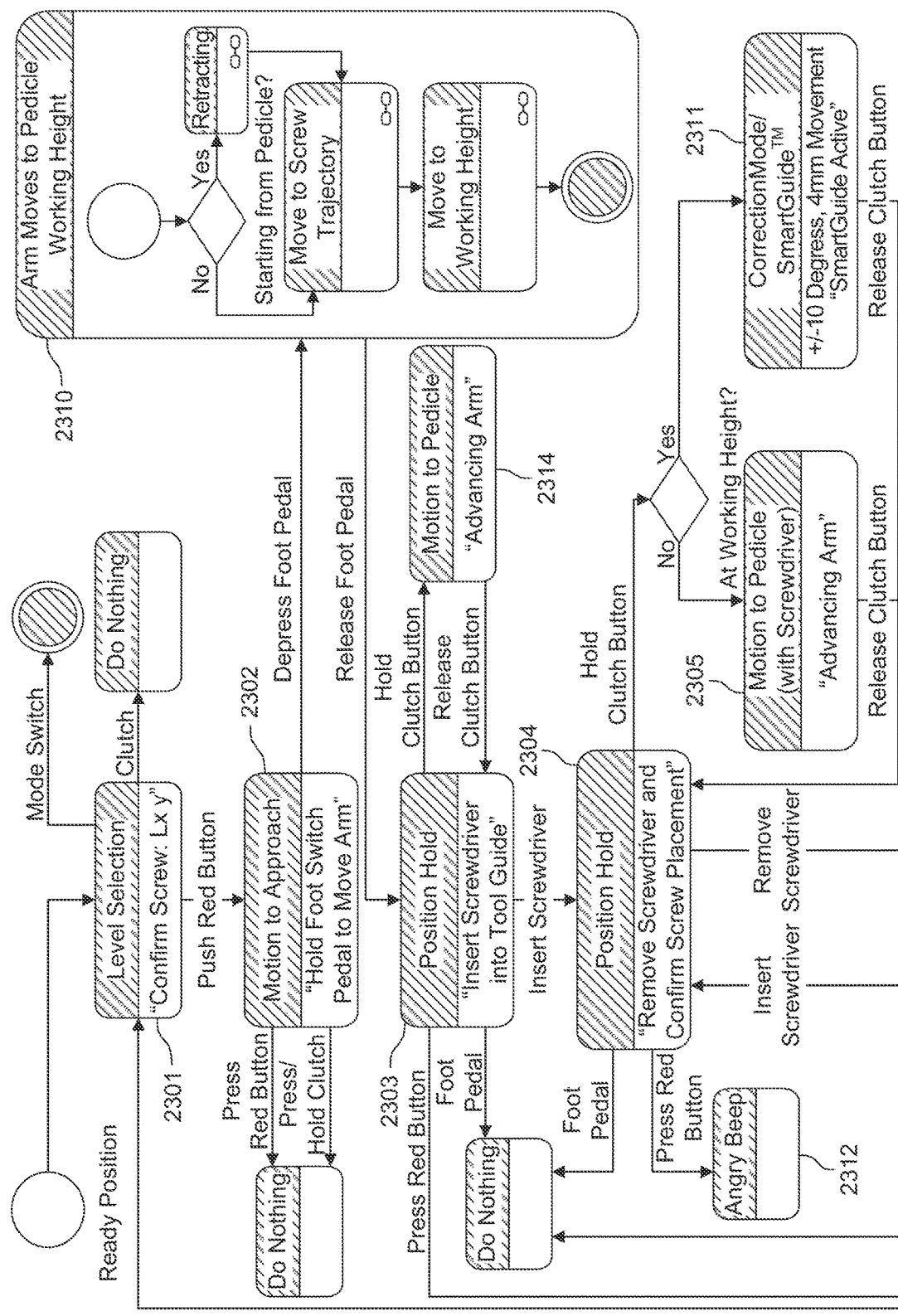
FIG. 23 shows an exemplary flow diagram of placing multiple screws using the robotic surgical system here.

FIG. 23 shows an exemplary diagram of workflow using the robotic surgical system 2211 disclosed herein for a surgical procedure, e.g., bone screw placement. Several steps or operations in FIG. 23 can correspond to different display/stages at the GUI 100 as shown in FIGS. 1-19 herein.

Referring to FIG. 23, in a particular embodiment, the surgical procedure may involve a vertebra level selection 2301. The user may be asked to confirm bone screw to be inserted or a vertebra location for screw insertion, e.g., L5, left. At this stage, holding a motion clutch button at the GUI or a physical button on the robotic arm may not actuate the robotic arm. Exemplary images at the GUI are shown in FIG. 4. If the user pushes the motion to approach button on the robotic arm or on the GUI, e.g., a red button, the user may approach the planned trajectory of the screw or the surgical site using the robotic arm 2302. The GUI 100 may provide instructive information to the user such as "hold foot pedal to move robotic arm." Exemplary images are shown in FIG. 6. The user can respond to the instructive information by providing a user input, e.g., depression and holding of the foot pedal to actuate automatic motion of the robotic arm to approach planned trajectory when distal aspect the robotic arm, e.g., tool holder 2216, reaches level of patient reference array 2105. Pressing the red button or the clutch button may not accurate the robotic arm at this stage. With a user depressing the foot pedal, the robotic arm 2211 may automatically or manually with the user's guidance move to a pre-determined pedicle screw working height 2310. Exemplary images at this step are shown in FIG. 6. At this step 2310, the robotic arm may be adjusted between the screw trajectory position and the pedicle screw working height in order to achieve satisfactory position or height 2310. Subsequently, the robotic arm may enter a position hold state 2303 when the foot pedal is released. The instructive information may assist the surgeon to insert screwdriver 110, 2217 into the tool guide 111, 2216. Exemplary images are shown in FIG. 7.

Figure 13:
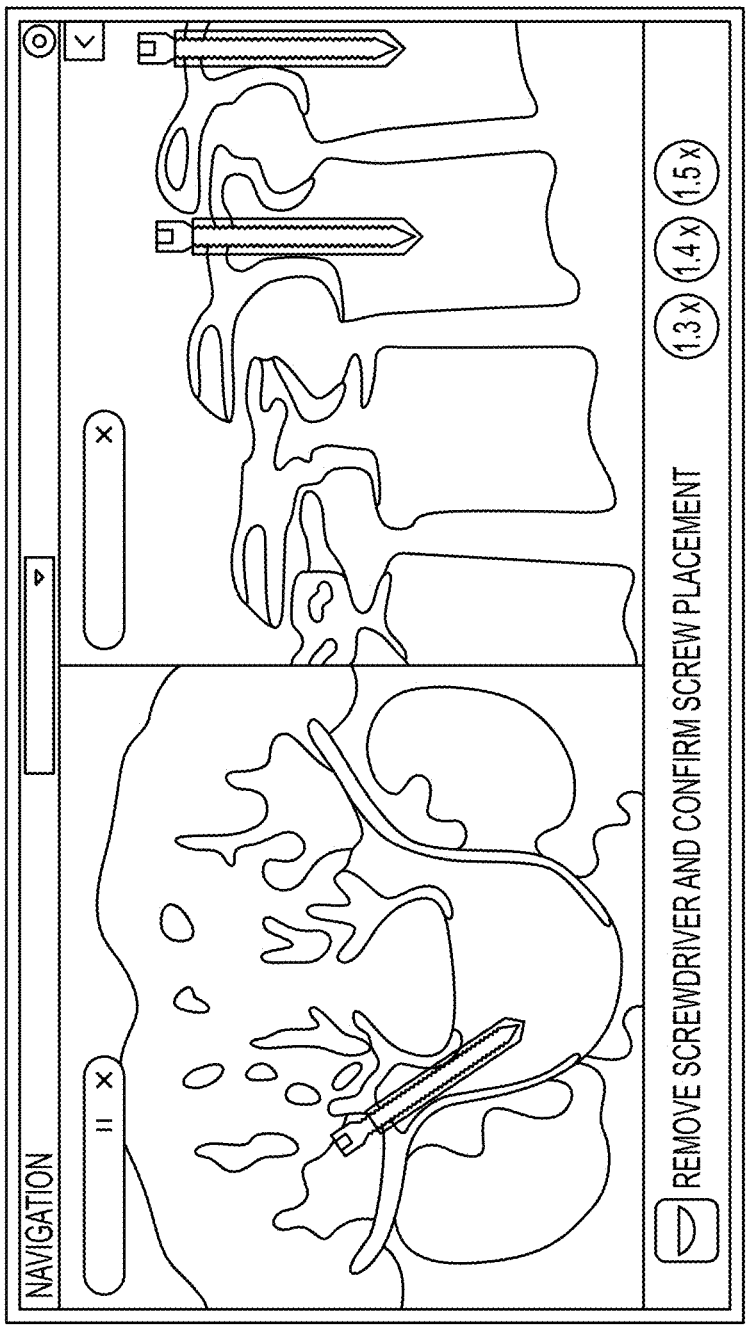
Figure 14:
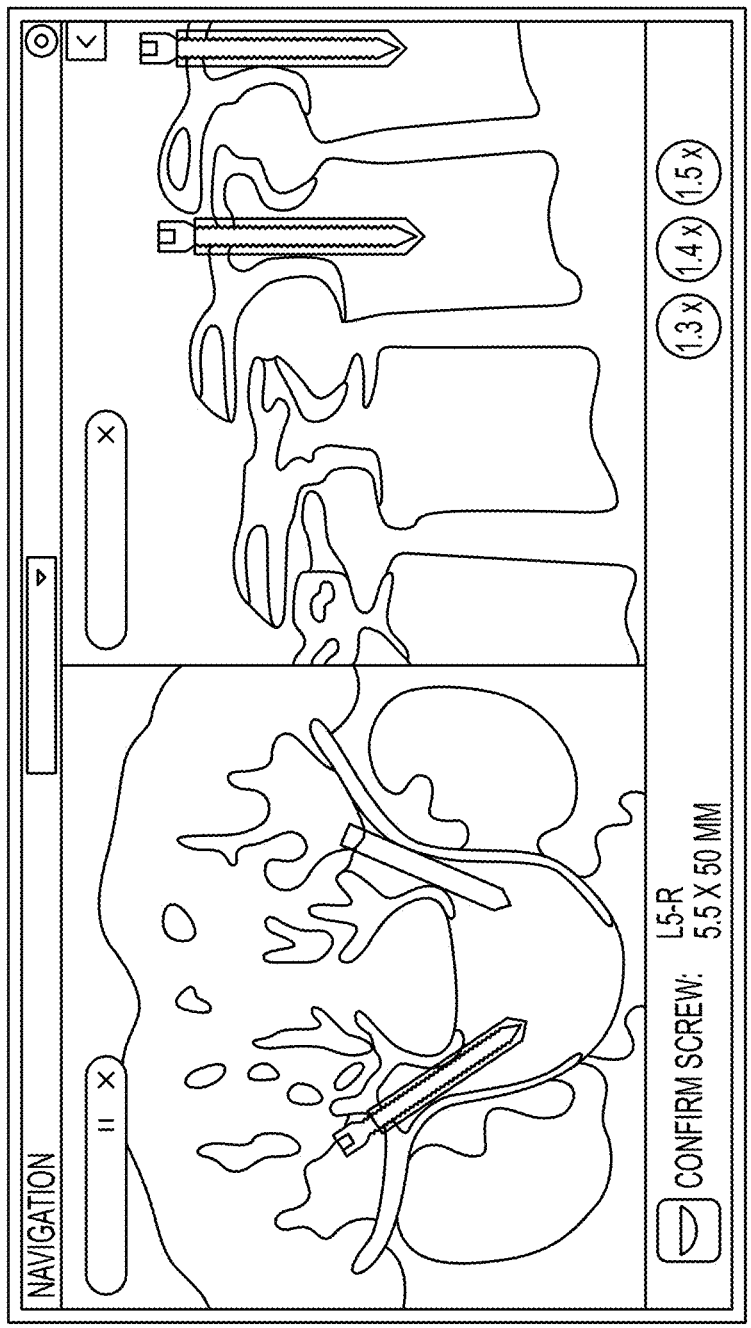
Figure 15:
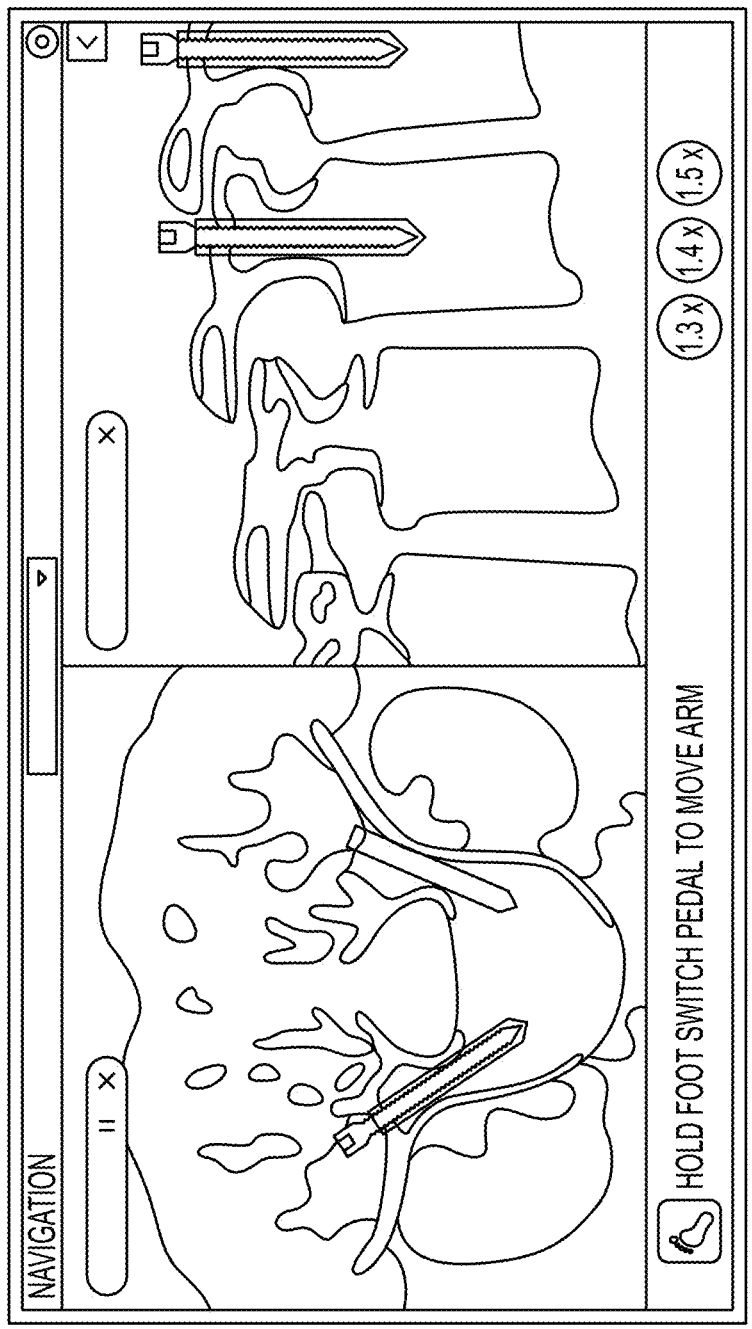
Figure 16:
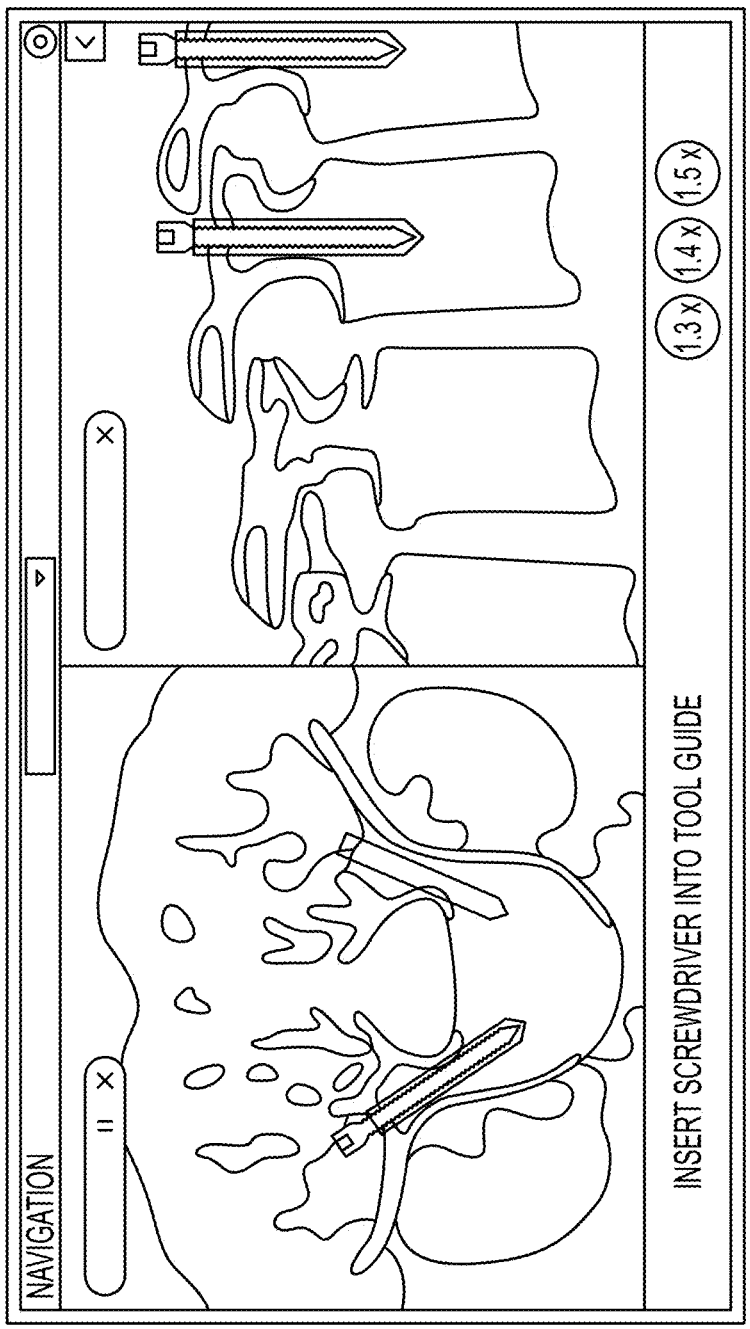
Figure 18:
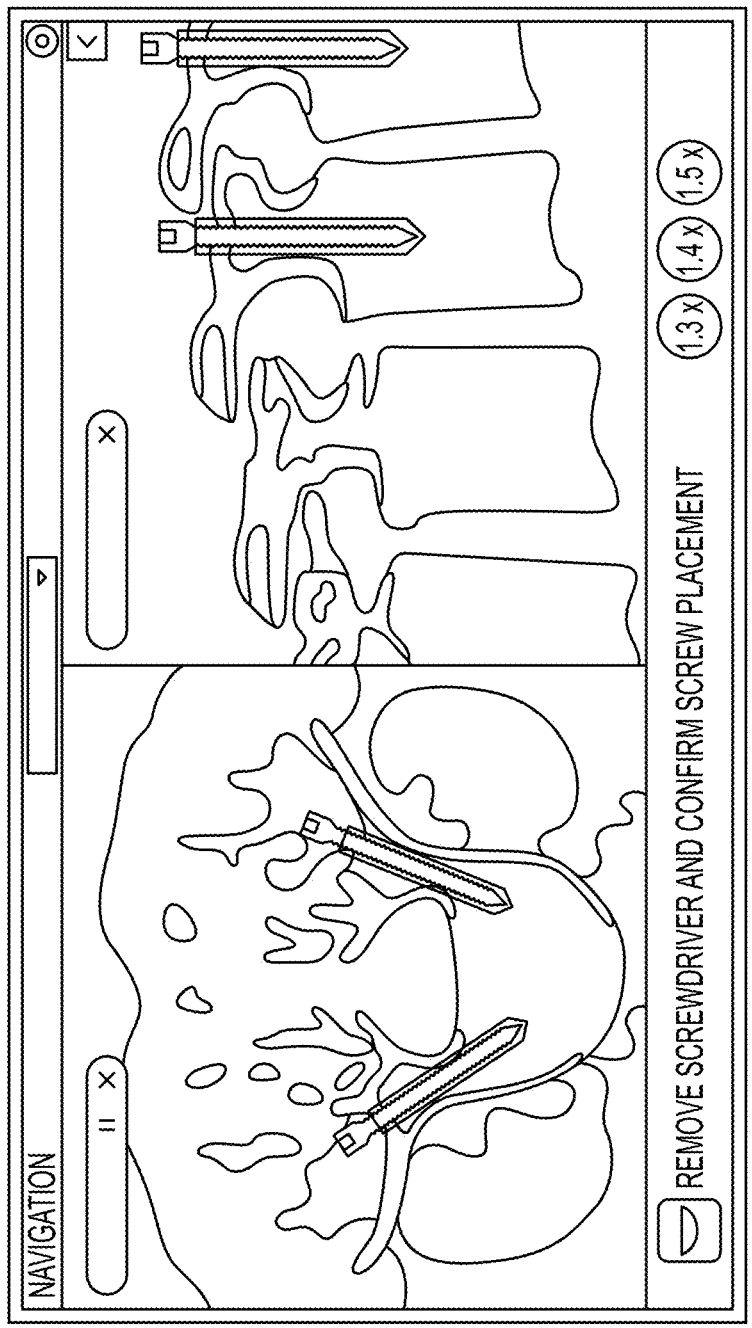

Continue referring to FIG. 23, when at the position hold state 2303, the user may hold the clutch button or release the clutch button to move or hold the robotic arm 2314. This can be used without the screwdriver to confirm or adjust the position of the robotic arm. After the robotic arm reaches a desired location, the user may manually insert the screwdriver with it securely locked to the distal end of the robotic arm as shown in FIGS. 21-22, and insert the pedicle screw. Exemplary images of screw placements are shown in FIG. 13. Afterward the screw placement is properly performed and confirmed, the screwdriver may be removed in a position hold stage 2304. In one or more steps during the procedure shown in FIG. 23, the robotic surgical system may provide visual or audio signal 2312 when the user's input, e.g., pressing a red button, pressing the clutch, etc., initiates no actuation of the robotic arm. Following a screw insertion, a different screw may be inserted again by repeating screwdriver insertion and the position hold step 2304, 2313. Exemplary images of the GUI are shown in FIGS. 9-10, and 14-15. Advancement of the robotic arm may be performed with the screw driver in place 2305 or without 2306 to tune the robotic arm position and/or the screw driver position relative to the screw placement trajectory. The robotic arm may switch between a correction mode or a fine movement mode 2311 and a position hold stage 2304 by providing a user input, e.g., hold or release of a clutch button, when the screw driver is at a predetermined pedicle working height. Exemplary image of the Smart Guide mode are shown in FIGS. 11-12. In some embodiments, the range of motion for the robotic arm in the fine movement mode can be predetermined by a user. For example, the robotic arm movement range can be restricted to a cone shape, e.g., for the about +/−4 mm and about +/−10 degrees either at a distal end of the robotic arm 2216 or at a distal end of the screw driver or other tool that may be securely attached to the robotic arm 2217. The user can select to start the motion of the robotic arm automatically. Alternatively, the user can further select to control the type or degree of motion of the robotic arm, e.g., "translate," "tilt," and/or "insertion." Exemplary images of screw placements are shown in FIGS. 18-19.

Figure 24:
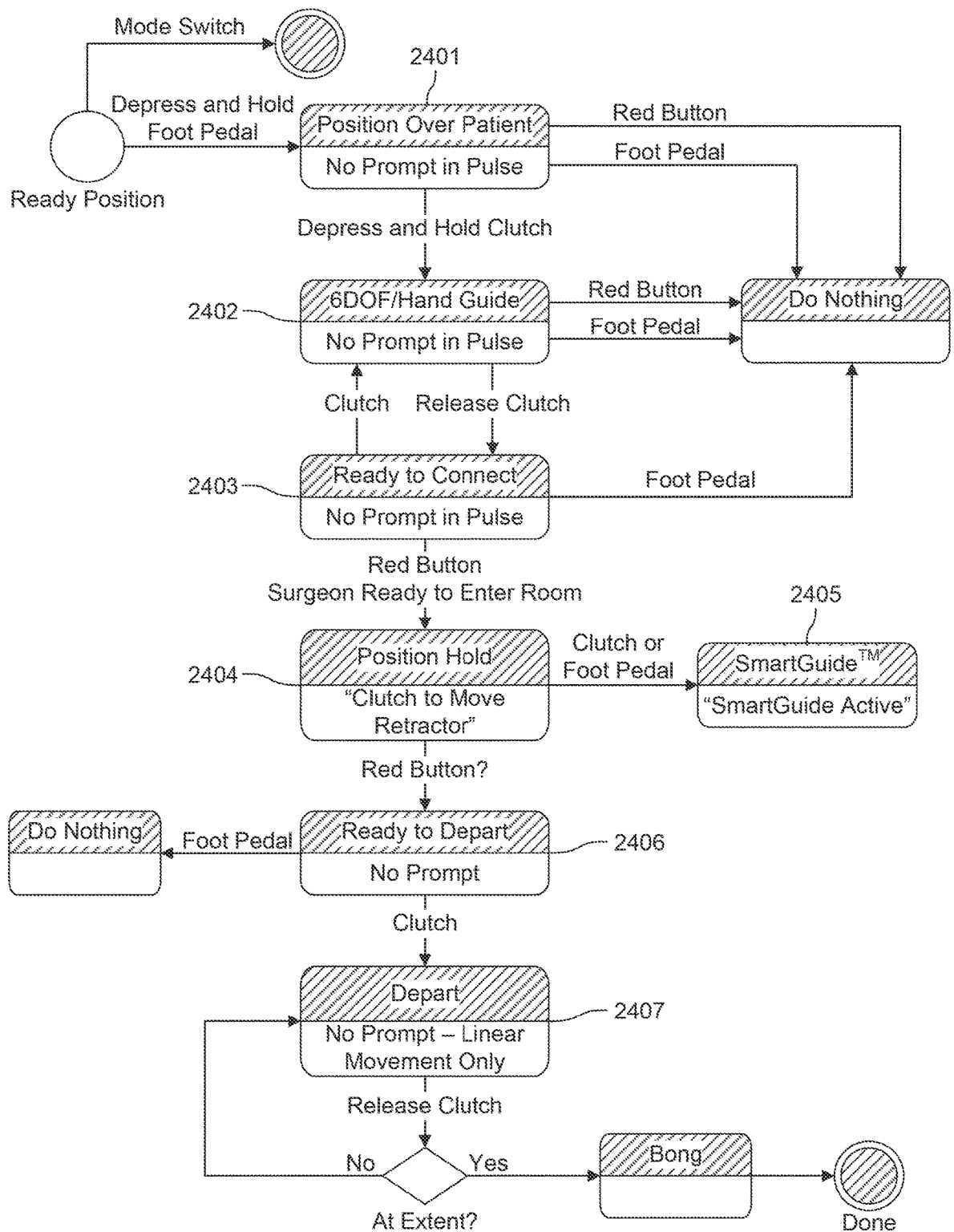
FIG. 24 shows an exemplary flow diagram of operating a surgical retractor using the robotic surgical system disclosed herein.
Figure 25:
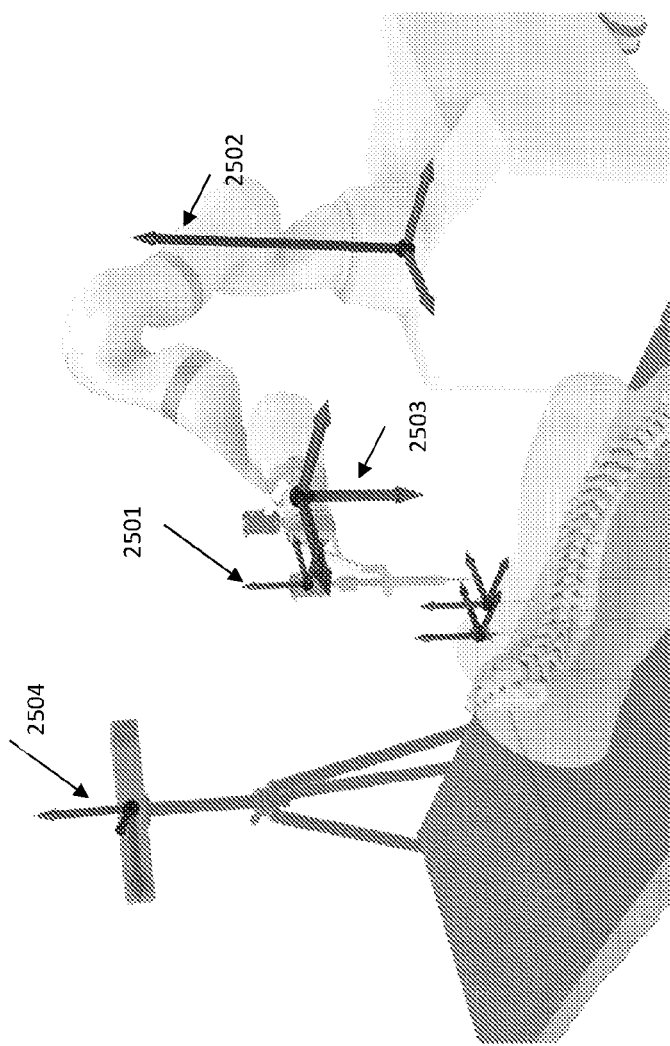
FIG. 25 shows an exemplary embodiment of the different coordinates with reference to the base of the robotic arm or with reference to the image capturing device, e.g., localizer, in accordance with embodiments herein.

Continuing referring to FIG. 23, when all screws are placed, the robotic arm can be retracted 2307 from the surgical site, move to a ready position that can be further away from the surgical site, and provide a cue for the user 2390 for completion of the procedure. [0086] FIG. 24 shows an exemplary diagram of workflow using the robotic surgical system 2101 disclosed herein for operating a surgical retractor, for example, in an Extreme Lateral Interbody Fusion (XLIF) procedure. In this particular embodiment, the surgeon may depress and hold an input device, e.g., foot pedal to allow positioning of the robotic arm over patient 2401. Such positioning can be automatically performed by the robotic arm 2211 or via hand-guiding by a user. At this step, the GUI 100, which is part of the digital processing device 2001, or the "Pulse" system, may not provide any user prompts. Alternatively, user prompt can indicate the status of the robotic arm 2211, e.g., place the robotic arm over the patient, or instructive information for the user, e.g., hand-guide to move the robotic arm to be over the patient. After the robotic arm is positioned over the patient 2401, if the user depresses and holds an input device, e.g., clutch, of the robotic arm 2211, the use can hand-guide the robotic arm with six degree of freedom 2402 to a ready position for connecting to a retractor 2403. Alternatively, the robotic arm may automatically move to the position for connecting to a retractor. The GUI 100 may display the current status of the robotic arm and/or the prompt for instructing the user to connect a retractor to the robotic arm. The user may push a red button on the robotic arm to put the robotic arm into a hold positon 2404, and connect a retractor to the distal end of the robotic arm. And the GUI may display "position hold," and/or "clutch to move retractor" after the retractor is connected 2404. When the user/surgeon provides an input at the clutch, foot pedal, or at the GUI, the robotic arm can enter the smart guide mode, and the GUI can be updated to display the status information as "Fine Movement Mode" Active, 2405. If a red button is pressed after position hold or smart guide state, the robotic arm may get ready to depart the surgical site 2406. The GUI may not display any information to indicate the departure of the robotic arm. Alternatively, the GUI may display information to indicate the departure. When the user provides an input such as pressing the clutch, the robotic arm can depart automatically from the surgical site and reach a predetermined location when it stops 2407 or when the user releases the clutch 2408. As another option, the robotic arm may depart based on user's hand guide. The robotic arm may provide an audio or visual signal 2408 when it is stopped. In one or more steps disclosed herein in FIG. 24, the robotic surgical system 2101 may also provide visual and audio cues in addition to the user prompts at the GUI 100. For example, after the robotic arm has been retracted back from the surgical site as the user depresses the clutch, the robotic arm may send an audio signal, e.g., bong, to indicate the robotic arm has been retracted back beyond a distance from the surgical site.

Robotic Arm Registration

In some embodiments, the robotic arm 2211 may be attached on a movable cart 2210 as shown in FIGS. 21-22. The base of the robotic arm does not move relative to the movable cart, therefore when the movable cart is parked and locked to the floor, e.g., wheels locked and stabilizing feet extended to floor, the base of the robotic arm cannot move relative to the floor. After the cart is parked, the robotic arm 2211, e.g., the distal portion of the arm 2212, can move in 3D relative to the base or the cart 2210, and the movement of the distal end of the robotic arm can be relative movement to the base of the robotic arm. In some embodiments, control of the robotic arm is performed by the digital processing device 2001 disclosed herein in a base-determined coordinate system relative to the base.

In some embodiments, the base-determined coordinate system is a coordinate system where the base, e.g., the center of the base is considered as the origin of the coordinate system, and a position of the distal end of the robotic arm 2216, 2217 may has a set of 3D coordinates 2501 $x_{arm1}$, $y_{arm1}$, $z_{arm1}$ relative to the origin. In some embodiments, the base-determined coordinate system is a coordinate system where the base, e.g., the center of the base has a set of 3D coordinates 2502 $x_{base}$, $y_{base}$, and $z_{base}$, relative to a selected origin, and the distal end of the arm, e.g., the center of the medial flange, may have another set of 3D coordinates 2503 $x_{arm1}$, $y_{arm1}$, $z_{arm1}$ relative to the same selected origin or to $x_{base}$, $y_{base}$, and $z_{base}$. The movement of robotic arm may be controlled by providing sets of 3D coordinate systems for its movement at specific time points.

In some embodiments, the base coordinate system disclosed herein is different from the imaging coordinate system used for the medical images of the anatomical features, and the tracking coordinate system used for tracking the tracking arrays attached to the patient, the surgical tools, and/or the robotic arm.

3D registration can be performed to register the imaging and the tracking coordinate systems. Such 3D registration information can be used to register the robotic arm to the tracking and the imaging coordinate systems.

In some embodiments, one or more tracking array can be attached at or near a distal end of the robotic arm. As shown in FIG. 22, in an exemplary embodiment, one tracking array 2218 is attached distal to the media flange 2215 and in close proximity to the tool guide 2216 for holding a surgical tool 2217. Another tracking array 2219 can attached to the surgical tool 2217. In a sense, the distal end of the robotic arm 2211 can be tracked equivalently as other surgical tools by the image capturing device 2102 as long as the tracking array(s) attached on the robotic arm are detectable to the image capturing device herein.

In some embodiments, the image capturing device 2102 is an infrared system that detects infrared light that may reflect from the tracking markers on a tracking array. With the tracking array attached on the robotic arm, a set of 3D coordinates for each tracking marker can be generated in a tracking coordinate system.

In some embodiments, the tracking-determined coordinate system is a coordinate system where the image capturing device, e.g., a point at the localizer, is considered as the origin of the coordinate system, and the position(s) of the distal end of the robotic arm may has a set of 3D coordinates $x_{arm2}$, $y_{arm2}$, $z_{arm2}$ relative to the origin. In some embodiments, the tracking determined coordinate system is a coordinate system where the image capturing device, e.g., the center of the localizer has a set of 3D coordinates 2504 $x_{localizer}$, $y_{localizer}$, and $z_{localizer}$ relative to a selected origin, and the distal end of the arm, e.g., the center of the medial flange, may have another set of 3D coordinates $x_{arm2}$, $y_{arm2}$, $z_{arm2}$, relative to the same selected origin or to $x_{localizer}$, $y_{localizer}$, and $z_{localizer}$. The movement of robotic arm in the tracking coordinate system may be determined by obtaining sets of 3D coordinate systems during its movement at specific time points.

In some embodiments, multiple points may be selected to register the base and the tracking coordinate system. In some embodiments, the multiple points may be identical to the points that are used to register the imaging coordinate system with the tracking coordinate system. In some embodiments, the registration between the base and tracking coordinate system is similar to the registration between the imaging and tracking coordinate system.

In some embodiments, 3D coordinates of the multiple points in the base and tracking coordinate systems can be used to register the two coordinate systems in 3D. In some embodiments, registration can be with 5 or 6 degree of freedom. In some embodiment, the registration can use at least 2, 3, 4, 5, or even more points in 3D, with 3 coordinates for each points. In some embodiments, among these multiple points, no 3 points are in a straight line in 3D.

In some embodiments, the registration of the two different coordinate systems in 3D involves a transformation matrix. In some embodiments, the transformation matrix may be a 4 by 4 matrix. In some embodiments, the transformation matrix is selected to be the one that transforms 3D coordinates in the base coordinate system to the corresponding 3D coordinate system in the tracking coordinate system, or vice versa, with an error below a pre-selected threshold. In some embodiments, the transformation matrix can be multiplied to one or more points in one coordinate system to transfer the point(s) to the other coordinate system.

In some embodiments, in the tracking coordinate system, the robotic arm is prescribed to move a distance along a specific direction to approach the surgical site. Such distance is also registered to the imaging system as the user may prescribe the distance in images of the surgical site, the surgical tool, and the robotic arm. In order to control the robotic arm in the base coordinate system, the prescribed distance (with its direction in 3D) in the tracking and imaging coordinate systems (registered in 3D) is transformed to the base coordinate system to be a transformed distance. The robotic arm can be controlled to move the transformed distance along the transformed direction in the base coordinate system.

Figure 27:
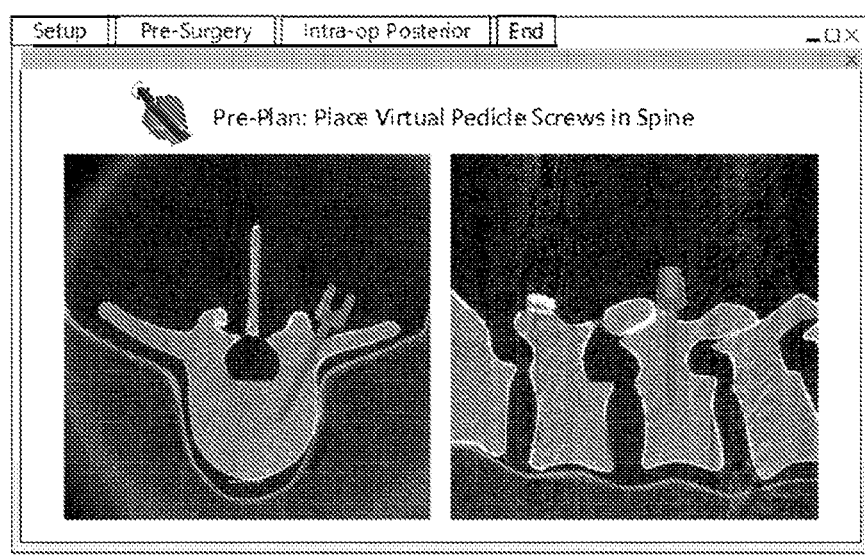
FIG. 27 shows an exemplary embodiment of 3D navigation of a surgical tool operated by the robotic arm using the systems and methods disclosed herein.

In a particular embodiment, as shown in FIG. 27, a surgeon can plan placement of a pedicle screw by placing a virtual screw in the images. The virtual screw is planned in the imaging coordinate system that is registered to the tracking coordinate system. In order to move the robotic arm to follow the planed screw trajectory, the digital processing device herein can register the tracking coordinate system and the base coordinate system as disclosed herein so that robotic arm movement registered to the surgical site and the planned trajectory in the tracking and imaging coordinate system. In this embodiment, the robotic arm is controlled in the base coordinate system relative to the base but still achieve the planed trajectory in the tracking and imaging coordinate systems.

Tracking Arrays

Disclosed herein are tracking arrays that can be used in image guided or computer assisted surgery. Disclosed herein are tracking arrays that can be used with a surgical navigation system for tracking medical instruments. The tracking arrays can be used to track or navigate instruments especially during a medical procedure or surgery.

The tracking array can be made of biocompatible materials including but not limited to plastic, polymer, metal, and alloy. The tracking array may be manufactured via 3D printing, molding or any other method of selection.

In some embodiments, the tracking array disclosed herein includes a 3D structure. The 3D structure includes a frame or an array body. The frame or array body may be of any 3D size and shape. The size and shape of the frame or array body in any spatial dimension(s) can be customized to accommodate the size and shape of the medical instruments to be attached thereto. In some embodiments, the size and shape may be determined to reduce the increase to the overall size of the object it is attached and the array yet still enabling coupling of the tracking array to the object, e.g., a vertebra, a surgical tool.

In some embodiments, the tracking array includes more than one tracking markers. The tracking markers can be located only on the outer surface of the tracking array. The relative position of two or more tracking markers, e.g., immediately adjacent markers, can be specifically determined so that each marker visible to the image capturing device can be uniquely identified. As such, the orientation and/or position of the medical instrument can be accurately determined based on the tracking information of the more than one markers.

In some embodiments, the relative position of one or more tracking markers to a reference point on the frame of the array (e.g., distal edge of the tracking array) is specifically determined so that, at a particular time point, at least 3 markers are visible and/or non-overlapping to the image capturing device no matter what the relative orientation of the instrument is in regard to the camera.

In some embodiments, the relative position of two or more tracking markers and/or the relative position of the marker(s) to the frame of the tracking array are pre-determined so that there are at least three markers visible and/or non-overlapping to the image capturing device no matter how the instrument is moved in 3D by a user during a medical procedure relative to the image capturing device. In some embodiments, a minimum number of 3 tracking markers are always detectable to the image capturing device with an arbitrary movement of the tracking array and the medical instrument relative to the image capturing device. The movement can be translation and/or rotation in 3D. In some embodiments, the tracking arrays herein are 360° arrays that enable detection of the instrument with any orientation or location in or near the patient. The plurality of tracking markers can be positioned on the outer surface so that at least 4, 5, 6, 7, 8, 9, or 10 of the plurality of tracking markers are visible to the image capturing device at a specific time point when the tracking array is rotated to an arbitrary rotation angle in three-dimension and/or moved relative to the image capturing device.

Since any two or three tracking markers are positioned uniquely relative to each other and/or to a reference point on the tracking array, when 3 tracking markers are detected, the surgical navigation system can figure out what these 3 tracking markers are and where they are located on the tracking array thereby generating accurate information of the location and orientation of the medical instrument.

In some embodiments, each tracking array has a unique arrangement of tracking markers when compared with other tracking arrays, so that when the surgical navigation system and/or the digital processing device recognizes a particular arrangement, the surgical navigation system can know which tracking array and which object is being tracked or navigated.

In some embodiments, the tracking markers include a reflective surface or a reflective coating that reflects light in a specific electromagnetic frequency range. In some embodiments, the tracking markers are spherical or sufficiently spherical. In some embodiments, the markers are identical in size and shape. In other embodiments, the markers can be of 3D shapes other than sphere and/or of sizes that are not identical. In some embodiments, two or more of the plurality of tracking markers comprise an identical shape, size, or both. In some embodiments, all of the plurality of tracking markers comprise an identical shape, size or both.

In some embodiments, at least part of the frame or array body is curved so that the tracking markers do not lie in a single flat two-dimensional plane, but instead, any two or three tracking markers can be in a two-dimensional plane different from a two-dimensional plane that another two or three tracking markers belong.

Figure 26:
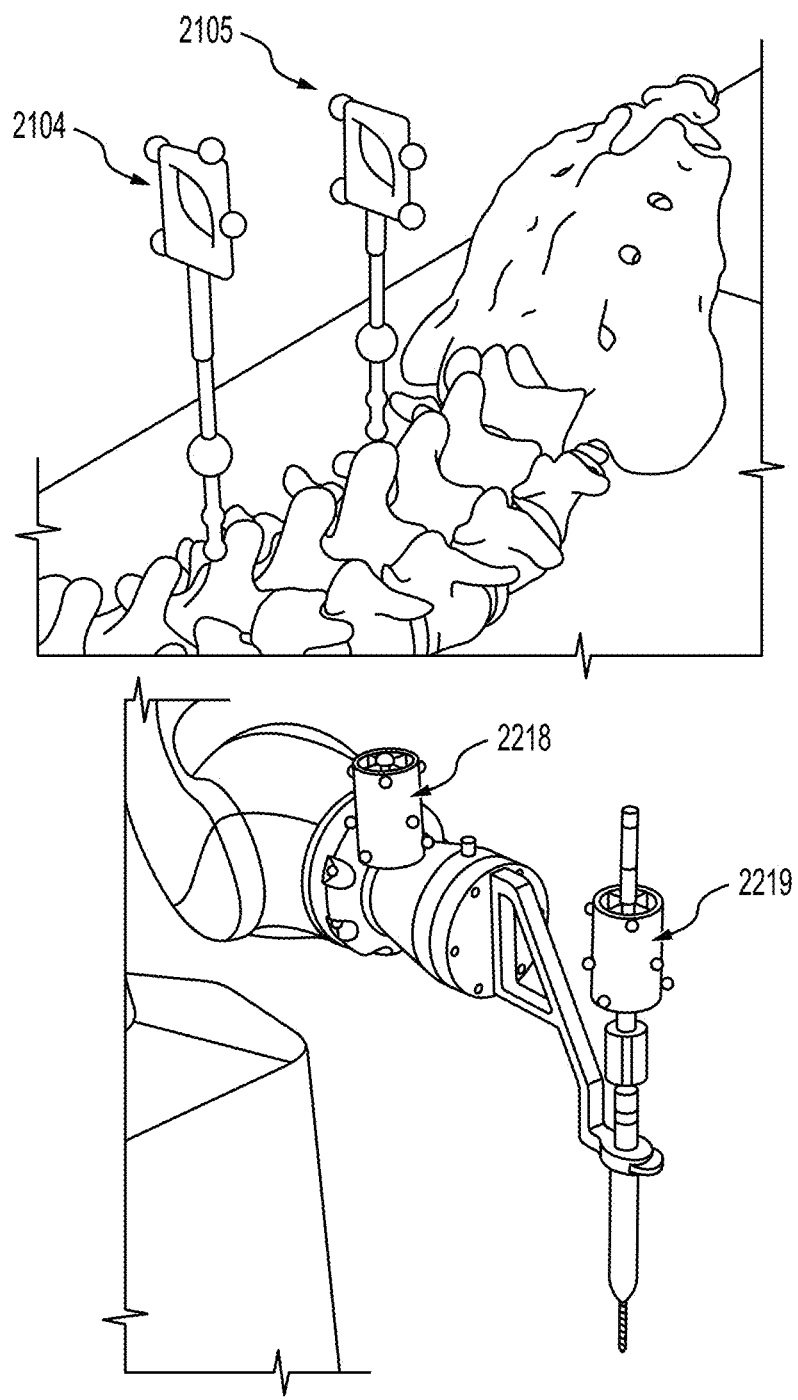
FIG. 26 shows exemplary embodiments of the tracking arrays, attached to the patient, the robotic arm, and/or the surgical tool, in accordance with embodiments herein.

In some embodiments, the tracking arrays 2104, 2105, 2218, 2219 disclosed herein can be attached to an anatomical feature of the subject, a surgical tool 2217, and/or a robotic arm 2211. FIG. 26 shows two tracking arrays 2104, 2105 attached to different vertebrae of the patient via an elongate pin that is visible to the C-arm. In the same embodiment, a tracking array is attached to a distal portion of the robotic arm 2218, and another tracking array 2219 is attached to a surgical too coupled to the tool guide at the distal end of the robotic arm.

Medical Instruments

In some embodiments, the tracking array can be attached to a medical instrument. More particularly, the tracking array disclosed herein can be attached to medical instruments for performing spinal surgeries. In some embodiments, the tracking array may be customized to be attached to a specific instrument. In some embodiments, the medical instrument can be any medical instrument with a proximal portion that is sized and shaped to be compatible with the tracking array. For example, the tracking array can be attached to a variety of disc preparation instruments for removal of the intervertebral disc or preparing the disc space for further operation. Such medical instruments can also be other instruments with a handle that has a proximal portion compatible to the cavity of the tracking array and the attachment feature in the tracking array.

In some embodiments, the medical instruments can be disc preparation tools or instruments, retractors, implant inserters, and dilators.

Image Capturing Devices

The systems and methods disclosed herein can include an image capturing device. The image capturing device can be any device that is capable of capturing data that can be used to generate a medical image of the subject. The image capture device can utilize one or more imaging modalities. For example, the image capturing device can include a Radiographic imaging device and an ultrasound imaging device. As another example, the image capture device can be an imaging scanner, such as an X-ray image intensifier or a C-arm. In some embodiments, the image capturing device can include a camera. The camera may utilize visible light, infrared light, other electro-magnetic waves in the spectrum, X-ray, or other sources.

In some embodiments, the image capturing device is in communication with the systems, methods, and media herein for data communication, or operational control of the image capturing device.

In some embodiments, the image capturing device includes an imaging sensor for detecting signal, e.g., visible light, x-ray, radio frequency (RF) pulses for generating the image(s). In some embodiments, the image capturing device includes one or more software modules for generating images using signal detected at the imaging sensor. In some embodiments, the image capturing device include a communication module so that it communicates data to the system, the digital processing device, a digital display, or any other devices disclosed herein.

The image capturing device can be any device that is capable of capturing information of the tracking markers. The image capture device can utilize one or more imaging modalities. In some embodiments, the image capturing device can include a camera. The camera may utilize visible light, infrared light, other electro-magnetic waves in the spectrum.

In some embodiments, the image capturing device is in communication with the surgical navigation system herein for data communication, or operational control of the image capturing device. Such communication may be unidirectional or bidirectional.

In some embodiments, the image capturing device includes an imaging sensor or a lens for detecting signal, e.g., infrared light. In some embodiments, the image capturing device includes one or more software modules for generating images using signal detected at the imaging sensor. In some embodiments, the image capturing device includes a communication module so that it communicates data to the system, the digital processing device, a digital display, or any other devices disclosed herein.

In some embodiments, the image capturing device includes one or more camera, lenses, or localizers. In some embodiments, the image capturing device includes a camera having at least two lenses at a fixed position relative to each other. In some embodiments, each lens detects a two-dimensional image and at least two two-dimensional images can be used to generate 3D information of the tracking markers. In some embodiments, the camera or lens detects reflective light from the tracking markers. The reflective light may be infrared light.

In some embodiments, the image capturing device includes a light source that transmits light to the tracking markers.

In some embodiments, the image capturing device can be free moving in 3D relative to the patient or the tracking array. The movement can include translation and/or rotation while the relative position of the two lenses within the device remain unaltered.

FIG. 21 shows two exemplary image capturing device, the first image capturing device is the C-arm 2103, the second is a dual localizer or a camera 2102.

Digital Processing Device

In some embodiments, the robotic surgical systems and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset.

In some embodiments, the digital processing device includes an input device to receive information from a user. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 20:
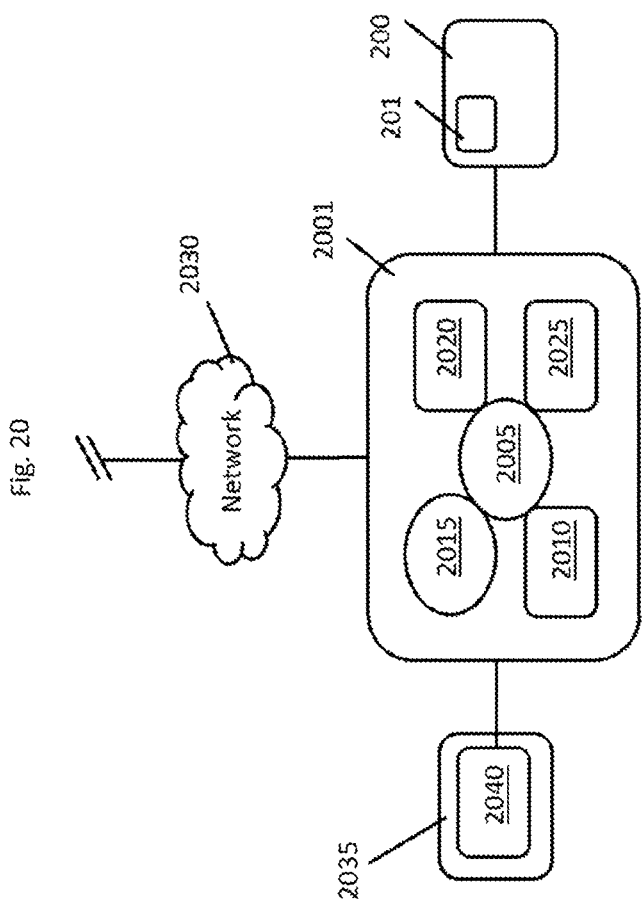
FIG. 20 shows an exemplary embodiment of the digital processing device of the surgical navigation system disclosed herein.

Referring to FIG. 20, in a particular embodiment, an exemplary digital processing device 2001 is programmed or otherwise configured to estimate visual acuity of a subject. The device 2001 can regulate various aspects of the algorithms and the method steps of the present disclosure. In this embodiment, the digital processing device 2001 includes a central processing unit (CPU, also "processor" and "computer processor" herein) 2005, which can be a single core or multi core processor, or a plurality of processors for parallel processing. The digital processing device 2001 also includes memory or memory location 2010 (e.g., random-access memory, read-only memory, flash memory), electronic storage unit 2015 (e.g., hard disk), communication interface 2020 (e.g., network adapter) for communicating with one or more other systems, and peripheral devices 2025, such as cache, other memory, data storage and/or electronic display adapters. The memory 2010, storage unit 2015, interface 2020 and peripheral devices 2025 are in communication with the CPU 2005 through a communication bus (solid lines), such as a motherboard. The storage unit 2015 can be a data storage unit (or data repository) for storing data. The digital processing device 2001 can be operatively coupled to a computer network ("network") 2030 with the aid of the communication interface 2020. The network 2030 can be the Internet, an internet and/or extranet, or an intranet and/or extranet that is in communication with the Internet. The network 2030 in some cases is a telecommunication and/or data network. The network 2030 can include one or more computer servers, which can enable distributed computing, such as cloud computing. The network 2030, in some cases with the aid of the device 2001, can implement a peer-to-peer network, which may enable devices coupled to the device 2001 to behave as a client or a server.

Continuing to refer to FIG. 20, the CPU 2005 can execute a sequence of machine-readable instructions, which can be embodied in a program or software. The instructions may be stored in a memory location, such as the memory 2010. The instructions can be directed to the CPU 2005, which can subsequently program or otherwise configure the CPU 2005 to implement methods of the present disclosure. Examples of operations performed by the CPU 2005 can include fetch, decode, execute, and write back. The CPU 2005 can be part of a circuit, such as an integrated circuit. One or more other components of the device 2001 can be included in the circuit. In some embodiments, the circuit is an application specific integrated circuit (ASIC) or a field programmable gate array (FPGA).

Continuing to refer to FIG. 20, the storage unit 2015 can store files, such as drivers, libraries and saved programs. The storage unit 2015 can store user data, e.g., user preferences and user programs. The digital processing device 201 in some cases can include one or more additional data storage units that are external, such as located on a remote server that is in communication through an intranet or the Internet.

Continuing to refer to FIG. 20, the digital processing device 2001 can communicate with one or more remote computer systems through the network 2030. For instance, the device 2001 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 2001, such as, for example, on the memory 2010 or electronic storage unit 2015. The machine executable or machine readable code can be provided in the form of software. During use, the code can be executed by the processor 2005. In some embodiments, the code can be retrieved from the storage unit 2015 and stored on the memory 2010 for ready access by the processor 2005. In some situations, the electronic storage unit 2015 can be precluded, and machine-executable instructions are stored on memory 2010.

The digital processing device 2001 can include or be in communication with an electronic display 2035 that comprises a user interface (UI) 2040 for providing, for example, means to accept user input from an application at an application interface. Examples of UI's include, without limitation, a graphical user interface (GUI) 100.

Non-Transitory Computer Readable Storage Medium

In some embodiments, the robotic surgical systems and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some embodiments, the program and instructions are permanently, substantially permanently, semi-permanently, or non-transitorily encoded on the media.

Computer Program

In some embodiments, the robotic surgical systems and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Software Modules

In some embodiments, the robotic surgical systems and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the robotic surgical systems and methods disclosed herein include one or more databases, or use of the same. In view of the disclosure provided herein, those of skill in the art will recognize that many databases are suitable for storage and retrieval of acuity chart, acuity subchart, preliminary information of a subject, chart data of a subject, input and/or output of algorithms herein etc. In various embodiments, suitable databases include, by way of non-limiting examples, relational databases, non-relational databases, object oriented databases, object databases, entity-relationship model databases, associative databases, and XML databases. Further non limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Although certain embodiments and examples are provided in the foregoing description, the inventive subject matter extends beyond the specifically disclosed embodiments to other alternative embodiments and/or uses, and to modifications and equivalents thereof. Thus, the scope of the claims appended hereto is not limited by any of the particular embodiments described herein. For example, in any method disclosed herein, the operations may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the systems, and/or devices described herein may be embodied as integrated components or as separate components.

We claim:

1. A robotic surgical system comprising:
a digital processing device comprising a processor, a memory, an operating system configured to perform executable instructions, a computer program including instructions executable by the digital processing device to create a graphical user interface (GUI) that is interactive with a user, and a digital display to display the GUI to the user,
wherein the GUI comprises a first image and a second image of a surgical site, the first image and the second image including an anatomical structure of a patient with different orientations, and wherein the GUI further comprises a representation of a surgical tool superimposed on the anatomical structure in the first image and the second image, the representation including color coding,
wherein the GUI comprises a status indicator bar, wherein the status indicator bar includes a first icon including instructive information related to the surgical tool and a second icon including status information of a surgical procedure using the surgical tool, wherein the GUI is configured to allow the user to interact directly with the first icon based on the instructive information or provide an input related to operation of the surgical tool based on the instructive information, and wherein the GUI is configured to provide an audio cue, a visual cue, or both simultaneously to the user based on the user's input, and configured to prompt the user to a next stage of the surgical procedure by changing the first icon, the second icon, or both if a status change criterion has been met; and
a robotic arm in communication with the digital processing device, wherein the robotic arm is controlled by the digital processing device to automatically move, approach the surgical tool, or move the surgical tool, based on the input provided by the user at the GUI until a pre-determined stopping criterion is met.

2. The system of claim 1, wherein the surgical tool is superimposed on the anatomical structure in full dimension and at a pre-determined opacity.

3. The system of claim 1, wherein the color coding comprises different colors for on-going, planned, and completed operation.

4. The system of claim 1, wherein the instructive information includes the color coding.

5. The system of claim 1, wherein the instructive information includes an operation of the surgical tool to be conducted.

6. The system of claim 1, wherein the instructive information includes graphical information or text related to selection or confirmation of a location, size, type of the surgical tool, or a combination thereof.

7. The system of claim 6, wherein the instructive information prompts the user to select or confirm location, size, type of the surgical tool, or a combination thereof.

8. The system of claim 7, wherein the first icon is configured to provide the instructive information for the user comprises one or more of:

interaction by the user with the GUI using a first input device; the interaction is configured to be reflected on the digital display; and the interaction is configured to be communicated to a digital processing device of the robotic surgical system or the robotic arm.

9. The system of claim 8, wherein the instructive information is configured to prompt the user to start operation of the surgical tool.

10. The system of claim 9, wherein the input to the robotic surgical system related to operation of the surgical tool in the surgical procedure based on the instructive information comprises one or more of:

the input at an actuation element using a second input device, wherein the actuation element is on the robotic arm or in communication with the robotic arm;

the input is configured to be reflected on the digital display; and the input is configured to communicated to a digital processing device of the robotic surgical system or the robotic arm.

11. The system of claim 10, wherein the second input device includes a foot pedal, a first button, or a second button.

12. The system of claim 11, wherein the input includes depression of the foot pedal, the first button, or the second button.

13. The system of claim 1, wherein the pre-determined stopping criterion comprises one or more of: a distance of at least a portion of the robotic arm to a reference point, wherein the reference point is at the anatomical structure of the patient, a patient reference array, or a tool tracking array.

14. The system of claim 1, wherein the status information includes the color coding.

15. The system of claim 1, wherein the visual cue includes a representation of the robotic arm in the first image, the second image, or both, and wherein the representation is continuously updated based on the location or movement of the robotic arm.

16. The system of claim 1, wherein the visual cue includes alternating color signal at the digital display when the robotic arm is in motion and static color signal when the robotic arm completes the motion.

17. The system of claim 1, wherein the audio cue includes alternating or static sound.

18. The system of claim 1, further comprises a skive detection unit and displaying a skive detection icon at the one or more stage of the surgical procedure, wherein the skive detection icon is color coded and includes a graphical meter that reflects level of skive at the skive detection unit.

* * * * *